United States Patent
Jin et al.

(10) Patent No.: US 12,108,745 B2
(45) Date of Patent: Oct. 8, 2024

(54) RAT MODEL OF IgA NEPHROPATHY INDUCED WITH A MULTIMERIC RECOMBINANT IgA FRAGMENT

(71) Applicant: Northwestern University, Evanston, IL (US)

(72) Inventors: Jing Jin, Hinsdale, IL (US); Xinfang Xie, Evanston, IL (US)

(73) Assignee: Northwestern University, Evanston, IL (US)

( * ) Notice: Subject to any disclaimer, the term of this patent is extended or adjusted under 35 U.S.C. 154(b) by 212 days.

(21) Appl. No.: 17/155,870

(22) Filed: Jan. 22, 2021

(65) Prior Publication Data

US 2021/0364500 A1 Nov. 25, 2021

Related U.S. Application Data

(60) Provisional application No. 62/964,748, filed on Jan. 23, 2020.

(51) Int. Cl.
| | |
|---|---|
| *A01K 67/027* | (2024.01) |
| *C07K 14/36* | (2006.01) |
| *C07K 16/00* | (2006.01) |
| *C07K 19/00* | (2006.01) |
| *G01N 33/50* | (2006.01) |

(52) U.S. Cl.
CPC ............ *A01K 67/027* (2013.01); *C07K 14/36* (2013.01); *C07K 16/00* (2013.01); *C07K 19/00* (2013.01); *G01N 33/5088* (2013.01); *A01K 2207/10* (2013.01); *C07K 2317/41* (2013.01); *C07K 2317/53* (2013.01)

(58) Field of Classification Search
CPC ............ A01K 67/027; A01K 2207/10; G01N 33/5088; C07K 16/00; C07K 19/00; C07K 14/36; C07K 2317/41; C07K 2317/53
USPC ............................ 800/9, 3; 530/387.3, 391.1
See application file for complete search history.

(56) References Cited

PUBLICATIONS

Cavagna, P., Stone, G., & Stanyon, R. (2002). Black rat (*Rattus rattus*) genomic variability characterized by chromosome painting. Mammalian Genome, 13(3), 157-163. (Year: 2002).*

Hass, I., Sbalqueiro, I. J., & Müller, S. (2008). Chromosomal phylogeny of four Akodontini species (*Rodentia, Cricetidae*) from Southern Brazil established by Zoo-FISH using Mus musculus (Muridae) painting probes. Chromosome Research, 16(1), 75-88. (Year: 2008).*

Floege, J., Moura, I. C., & Daha, M. R. (Jul. 2014). New insights into the pathogenesis of IgA nephropathy. In Seminars in immunopathology (vol. 36, No. 4, pp. 431-442). Springer Berlin Heidelberg. (Year: 2014).*

Snoeck, V., Peters, I. R., & Cox, E. (2006). The IgA system: a comparison of structure and function in different species. Veterinary research, 37(3), 455-467. (Year: 2006).*

Floege, J., Moura, I. C., & Daha, M. R. (Jul. 2014). New insights into the pathogenesis of IgA nephropathy. In Seminars in immunopathology (vol. 36, No. 4, pp. 431-442). Springer Berlin Heidelberg., p. 433 (Year: 2014).*

Yu, K., Liu, C., Kim, B. G., & Lee, D. Y. (2015). Synthetic fusion protein design and applications. Biotechnology advances, 33(1), 155-164. (Year: 2015).*

"daily"—definition—Merriam Webster.com, 2023.*

Wyatt R.J., et al., "IgA nephropathy", N Engl J Med, 368(25), pp. 2402-2414, 2013.

Lai K.N., et al., "IgA nephropathy", Nat Rev Dis Primers, 2: 16001, 2016.

Roberts I.S. "Pathology of IgA nephropathy", Nat Rev Nephrol, 10: 445-454, 2014.

Bellur S.S., et al. "Immunostaining findings in IgA nephropathy: correlation with histology and clinical outcome in the Oxford classification patient cohort", Nephrol Dial Transplant, 26: 2533-2536, 2011.

Suzuki K., et al. "Incidence of latent mesangial IgA deposition in renal allograft donors in Japan", Kidney Int, 63: 2286-2294, 2003.

Waldherr R., et al. "Frequency of mesangial IgA deposits in a non-selected autopsy series", Nephrol Dial Transplant, 4: 943-946, 1989.

Nakazawa S., et al. "Difference in IgA1 O-glycosylation between IgA deposition donors and IgA nephropathy recipients", Biochem Biophys Res Commun, 508: 1106-1112, 2019.

Gaber L.W., et al. "Prevalence, Characteristics, and Outcomes of Incidental IgA Glomerular Deposits in Donor Kidneys", Kidney Int Rep, 5: 1914-1924, 2020.

Hiki Y., et al. "O-linked oligosaccharide on IgA1 hinge region in IgA nephropathy", Fundamental study for precise structure and possible role. Contrib Nephrol, 111: 73-84, 1995.

Novak J., et al. "Aberrant Glycosylation of the IgA1 Molecule in IgA Nephropathy", Semin Nephrol, 38: 461-476, 2018.

Novak J., et al. "IgA nephropathy and Henoch-Schoenlein purpura nephritis: aberrant glycosylation of IgA1, formation of IgA1-containing immune complexes, and activation of mesangial cells", Contrib Nephrol, 157: 134-138, 2007.

Suzuki H., et al. "IgA1-secreting cell lines from patients with IgA nephropathy produce aberrantly glycosylated IgA1", J Clin Invest, 118: 629-639, 2008.

(Continued)

*Primary Examiner* — Anne Marie S Wehbe
(74) *Attorney, Agent, or Firm* — Benesch Friedlander Coplan & Aronoff LLP

(57) ABSTRACT

Recombinant poly-IgA oligomers that form high-order oligomers resembling poly-IgA of IgA nephropathy are provided. Injection of recombinant IgA oligomers in an animal model produces prominent renal glomerular mesangial deposition of recombinant poly IgA oligomer, as in IgA nephropathy patients. Thus, producing a model of IgAN pathology that is able to provide screening and evaluation of therapeutic drugs and diagnostic tests.

Figure 1D:
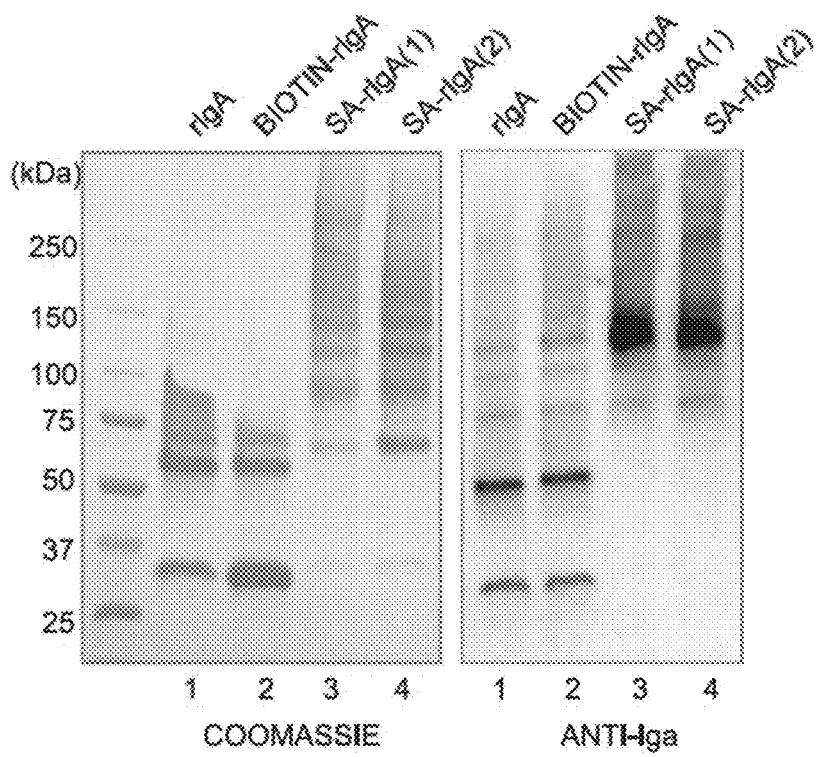

8 Claims, 27 Drawing Sheets
Specification includes a Sequence Listing.

(56) References Cited

PUBLICATIONS

Novak J., et al. "IgA glycosylation and IgA immune complexes in the pathogenesis of IgA nephropathy", Semin Nephrol, 28: 78-87, 2008.
Barratt J., et al. "Glomerular disease: sugars and immune complex formation in IgA nephropathy", Nat Rev Nephrol, 5: 612-614, 2009.
Tomana M., et al. "Circulating immune complexes in IgA nephropathy consist of IgA1 with galactose-deficient hinge region and antiglycan antibodies", J Clin Invest, 104: 73-81, 1999.
Sumiyama K., et al. "Adaptive evolution of the IgA hinge region in primates. Mol Biol Evol", 19: 1093-1099, 2002.
Suzuki H., et al. "Murine Models of Human IgA Nephropathy", Semin Nephrol, 38: 513-520, 2018.
Imai H., et al. "Spontaneous glomerular IgA deposition in ddY mice: an animal model of IgA nephritis", Kidney Int, 27: 756-761, 1985.
Coppo R., et al. "Gluten-induced experimental IgA glomerulopathy", Lab Invest, 60: 499-506, 1989.
Rostoker G., et al. "IgA antigliadin antibodies as a possible marker for IgA mesangial glomerulonephritis in adults with primary glomerulonephritis", N Engl J Med, 320: 1283-1284, 1989.
Pestka J.J., et al. "Dysregulation of IgA production and IgA nephropathy induced by the trichothecene vomitoxin", Food Chem Toxicol, 27: 361-368, 1989.
Marquina R., et al. "Inhibition of B cell death causes the development of an IgA nephropathy in (New Zealand white x C57BL/6)F(1)-bcl-2 transgenic mice", J Immunol, 172: 7177-7185, 2004.
Wang J., et al. "Dysregulated LIGHT expression on T cells mediates intestinal inflammation and contributes to IgA nephropathy", J Clin Invest, 113: 826-835, 2004.
McCarthy D.D., et al. "BAFF induces a hyper-IgA syndrome in the intestinal lamina propria concomitant with IgA deposition in the kidney independent of LIGHT", Cell Immunol, 241: 85-94, 2006.
Launay P., et al. "Fcalpha receptor (CD89) mediates the development of immunoglobulin A (IgA) nephropathy (Berger's disease), Evidence for pathogenic soluble receptor-Iga complexes in patients and CD89 transgenic mice", J Exp Med, 191: 1999-2009, 2000.
Berthelot L., et al. "Transglutaminase is essential for IgA nephropathy development acting through IgA receptors", J Exp Med, 209: 793-806, 2012.
Floege J. "Fatal Attraction: Immunoglobulin A and the Glomerular Mesangium", J Am Soc Nephrol, 30: 1139-1141, 2019.
Monteiro R.C., et al. "IgA Fc receptors", Annu Rev Immunol, 21: 177-204, 2003.
Monteiro R.C., et al. "Pathogenic significance of IgA receptor interactions in IgA nephropathy", Trends Mol Med, 8: 464-468, 2002.
Floege J. et al. "New insights into the pathogenesis of IgA nephropathy", Semin Immunopathol, 36: 431-442, 2014.
Ben Mkaddem S., et al. "Anti-inflammatory role of the IgA Fc receptor (CD89): from autoimmunity to therapeutic perspectives", Autoimmun Rev, 12: 666-669, 2013.
Boyd J.K., et al. "Immune complex formation in IgA nephropathy: CD89 a 'saint' or a 'sinner'?" Kidney Int, 78: 1211-1213, 2010.
Maruoka T., et al., "Identification of the rat IgA Fc receptor encoded in the leukocyte receptor complex", Immunogenetics, 55: 712-716, 2004.
Mestecky J., et al., "IgA nephropathy: molecular mechanisms of the disease", Annu Rev Pathol, 8: 217-240, 2013.
Fairhead M. et al., "Site-specific biotinylation of purified proteins using BirA", Methods Mol Biol, 1266: 171-184, 2015.
Brandtzaeg P. et al., Direct evidence for an integrated function of J chain and secretory component in epithelial transport of immunoglobulins, Nature, 311: 71-73, 1984.
Van der Boog P.J., et al., "Role of macromolecular IgA in IgA nephropathy", Kidney Int, 67: 813-821, 2005.
Morton H.C., et al., "Structure and function of human IgA Fc receptors (Fc alpha R)", Crit Rev Immunol, 16: 423-440, 1996.
Kitov P.I., "Bundle DR On the nature of the multivalency effect: a thermodynamic model", J Am Chem Soc, 125: 16271-16284, 2003.
Tan Y., et al., "Complement in glomerular diseases", Nephrology (Carlton), 23 Suppl 4: 11-15, 2018.
Thurman J.M., et al., "All Things Complement", Clin J Am Soc Nephrol, 11: 1856-1866, 2016.
Sancho J., et al., "The importance of the Fc receptors for IgA in the recognition of IgA by mouse liver cells: its comparison with carbohydrate and secretory component receptors", Immunology, 57: 37-42, 1986.
Yamaji K., et al., "The kinetics of glomerular deposition of nephritogenic IgA", PLoS One, 9: e113005, 2014.
Wang Y., et al., "Binding capacity and pathophysiological effects of IgA1 from patients with IgA nephropathy on human glomerular mesangial cells", Clin Exp Immunol, 136: 168-175, 2004.
Zhu L., et al., "Synergistic effect of mesangial cell-induced CXCL1 and TGF-beta1 in promoting podocyte loss in IgA nephropathy", PLoS One, 8: e73425, 2013.
Tortajada A., et al., "The role of complement in IgA nephropathy", Mol Immunol, 114: 123-132, 2019.
Maillard N., et al., "Current Understanding of the Role of Complement in IgA Nephropathy", J Am Soc Nephrol, 26: 1503-1512, 2015.
Silva F.G., et al., "Disappearance of glomerular mesangial IgA deposits after renal allograft transplantation", Transplantation, 33: 241-246, 1982.
Suzuki H., et al., "Aberrantly glycosylated IgA1 in IgA nephropathy patients is recognized by IgG antibodies with restricted heterogeneity", J Clin Invest, 119: 1668-1677, 2009.
Suzuki H., et al., "The pathophysiology of IgA nephropathy", J Am Soc Nephrol, 22: 1795-1803, 2011.
Abbad L., et al., "Food antigens and Transglutaminase 2 in IgA nephropathy: Molecular links between gut and kidney", Mol Immunol, 121: 1-6, 2020.
Shimozato S., et al., "Serum under-galactosylated IgA1 is increased in Japanese patients with IgA nephropathy", Nephrol Dial Transplant, 23: 1931-1939, 2008.
Zhao N., et al., "The level of galactose-deficient IgA1 in the sera of patients with IgA nephropathy is associated with disease progression", Kidney Int, 82: 790-796, 2012.
Sofue T., et al., "Latent IgA deposition from donor kidneys does not affect transplant prognosis, irrespective of mesangial expansion", Clin Transplant, 27 Suppl 26: 14-21, 2013.
Chen A., et al., "IgA nephropathy: clearance kinetics of IgA-containing immune complexes," Semin Immunopathol, 40: 539-543, 2018.
Xie X., et al., "Plasma Exchange as an Adjunctive Therapy for Crescentic IgA Nephropathy", Am J Nephrol, 44: 141-149, 2016.
Wyld M.L., et al., "Recurrent IgA Nephropathy After Kidney Transplantation", Transplantation, 100: 1827-1832, 2016.
Takahata A., et al., "Crucial Role of AIM/CD5L in the Development of Glomerular Inflammation in IgA Nephropathy", J Am Soc Nephrol, 31: 2013-2024, 2020.
Kawata N., et al., "Proteomics of human glomerulonephritis by laser microdissection and liquid chromatography-tandem mass spectrometry", Nephrology (Carlton), 25: 351-359, 2020.
Kojima S., et al., "Proteomic analysis of whole glomeruli in patients with IgA nephropathy using microsieving", Am J Nephrol, 39: 36-45, 2014.
Rops A., et al., "Interleukin-6 is essential for glomerular immunoglobulin A deposition and the development of renal pathology in Cd37-deficient mice", Kidney Int, 93: 1356-1366, 2018.
Makita Y., et al., "TLR9 activation induces aberrant IgA glycosylation via APRIL- and IL-6-mediated pathways in IgA nephropathy", Kidney Int, 97: 340-349, 2020.
Schreiber A., et al., "Transcutaneous measurement of renal function in conscious mice", Am J Physiol Renal Physiol 303, F783-788 (2012).
Moldoveanu, Z. et al. "Patients with IgA nephropathy have increased serum galactose deficient IgA1 levels" Kidney Int, 71:1148-1154, 2007.

(56) References Cited

PUBLICATIONS

Allen, A.G. et al "Galactosylation of N and G-linked carbohydrate moieties of IgA1 and IgG in IgA nephropathy" Clin Exp Immunol, 100: 470-474, 1995.

* cited by examiner

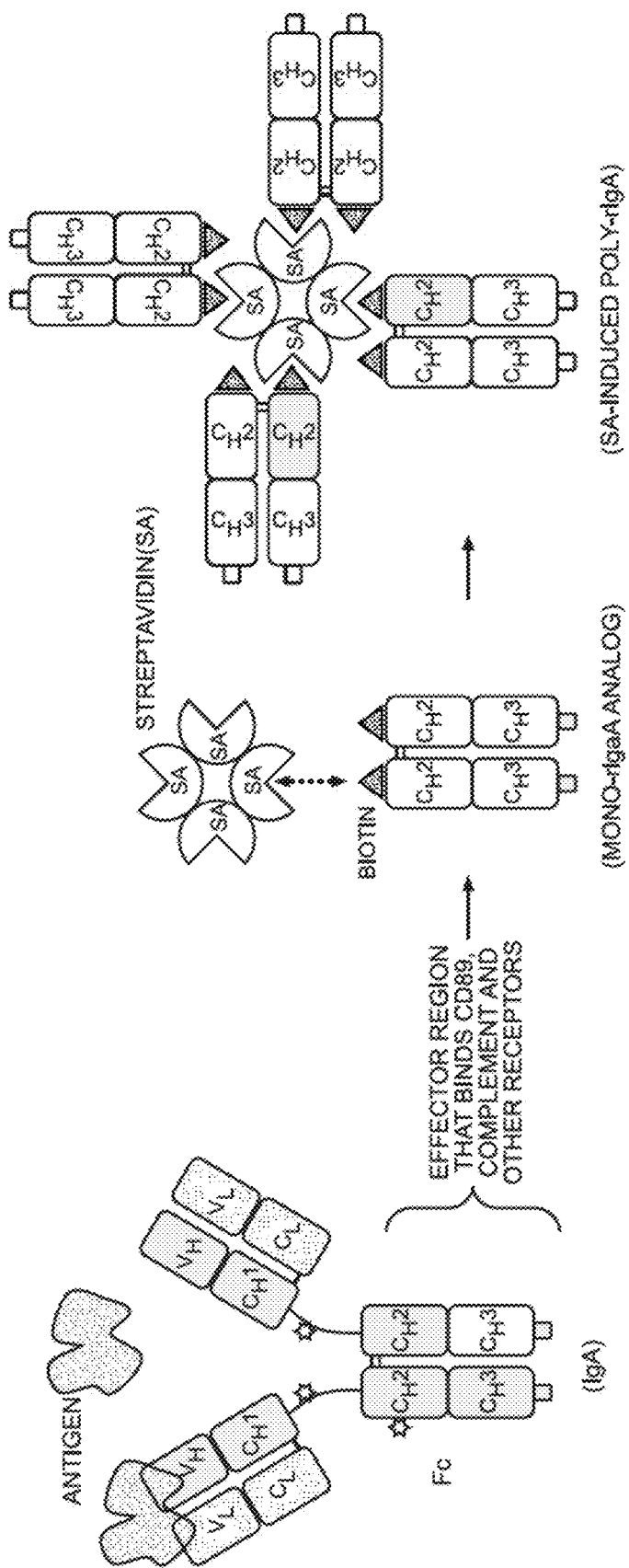

POLY-rIgA:Col4A1:DAPI

POLY-rIgA:Col4A1:DAPI

POLY-rIgA:Col4A1:DAPI

POLY-rIgA:Col4A1:DAPI

IF: POLY-rIgA

POLY-rIgA:DAPI

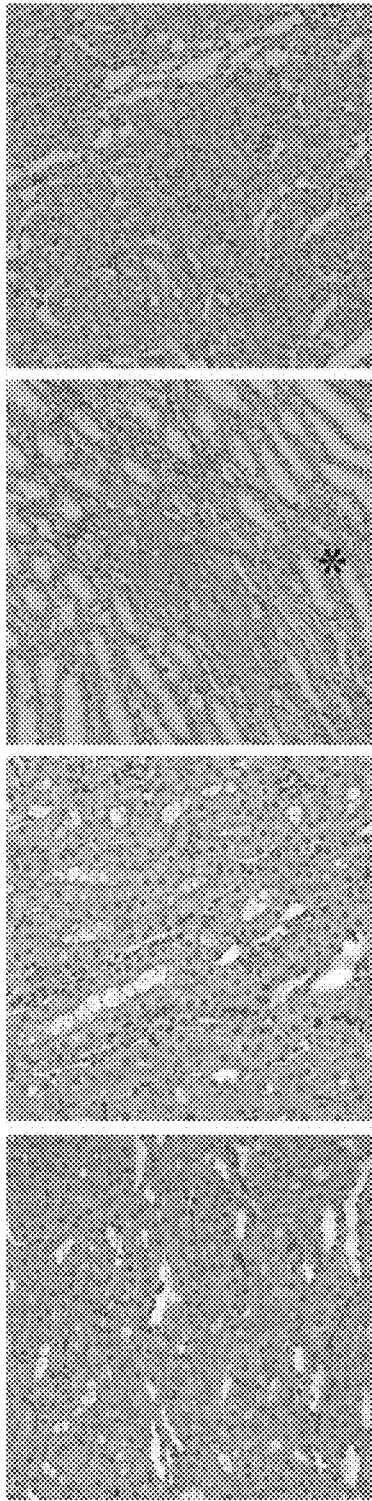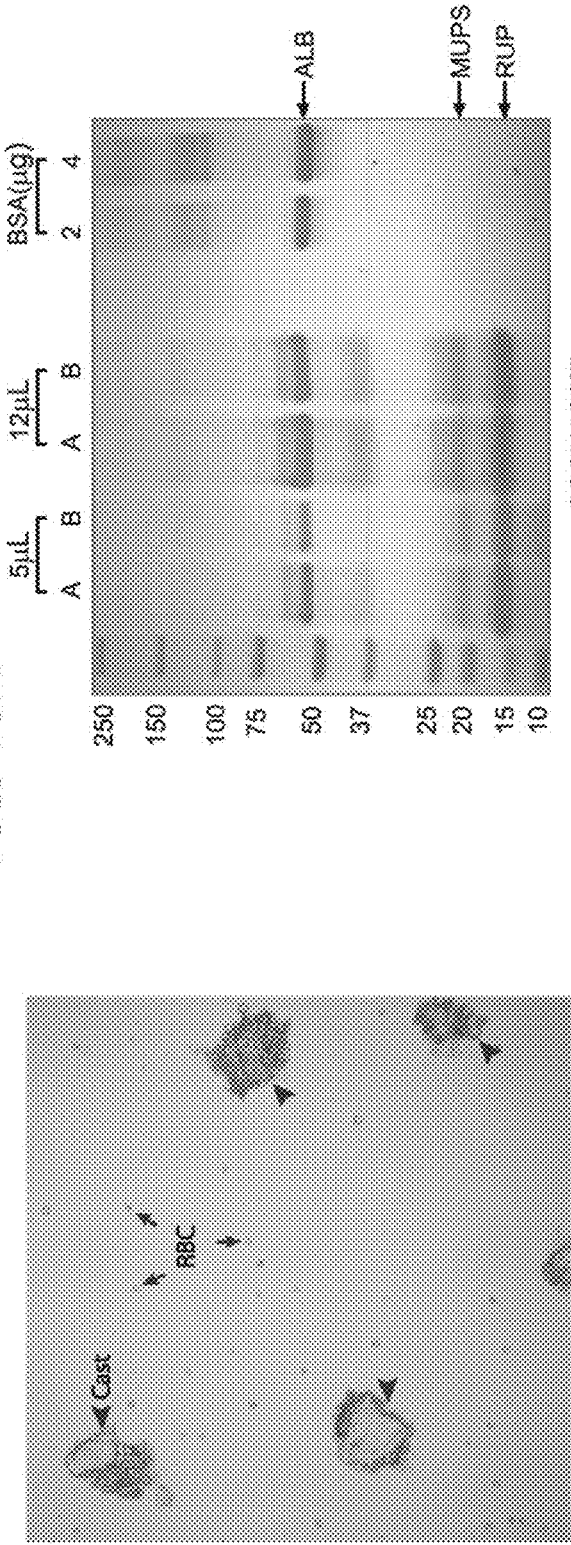
FIG. 16A
FIG. 16B
FIG. 16C

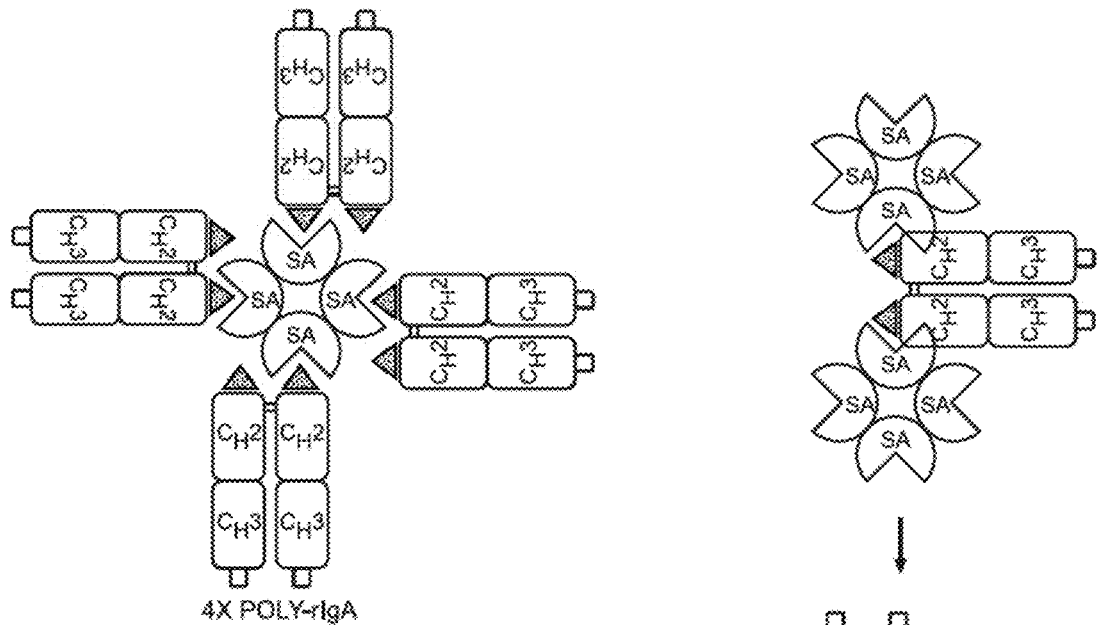
FIG. 20A
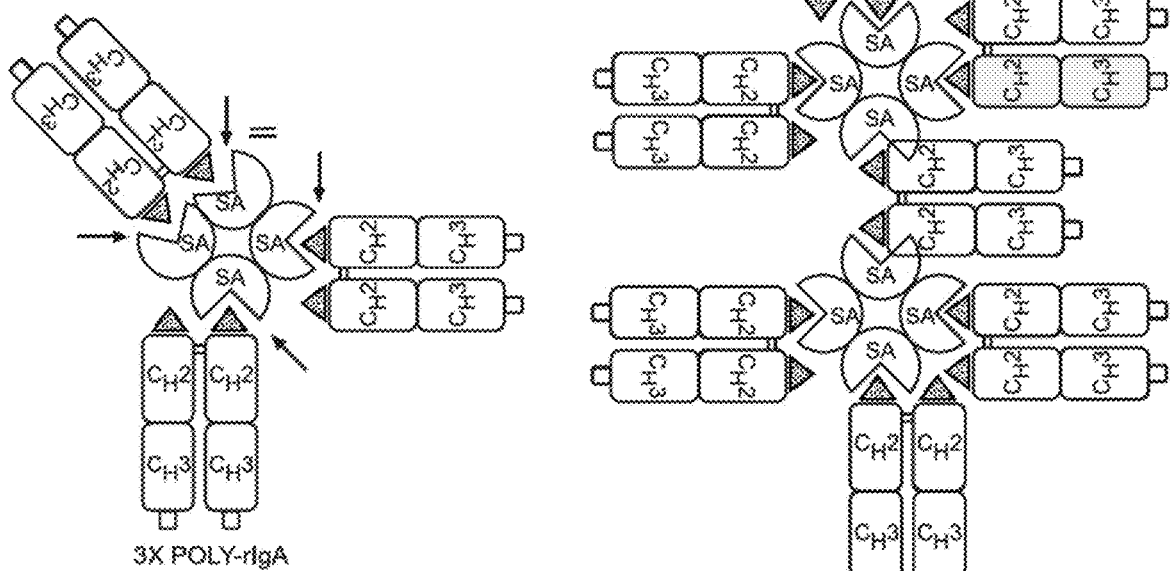
FIG. 20B
FIG. 20C

RAT MODEL OF IgA NEPHROPATHY INDUCED WITH A MULTIMERIC RECOMBINANT IgA FRAGMENT

CROSS-REFERENCE TO RELATED APPLICATIONS

This application claims priority to U.S. Provisional Patent Application No. 62/964,748, filed Jan. 23, 2020, which is incorporated by reference herein in its entirety.

TECHNICAL FIELD

Methods and compositions relating to a kidney disease animal model of IgA nephropathy.

REFERENCE TO A SEQUENCE LISTING

The instant application contains a Sequence Listing which has been filed electronically in ASCII format as 47460-120_ST25.txt created on Jan. 20, 2021 and is 2,782 bytes in size and is hereby incorporated by reference in its entirety.

BACKGROUND

IgA nephropathy (IgAN), also known as Berger's disease, is the most common form of glomerular nephritis. It has the pathologic feature of immunoglobulin IgA deposition in the glomerular mesangium, leading to chronic inflammation of the kidney. Many IgAN patients follow a course of gradual decline of their kidney function over years as measured by glomerular filtration rate. Some patients eventually reached end-stage renal disease that requires dialysis or renal transplantation.

The cause of IgAN is unknown and there are no specific treatments to the disease. In terms of IgAN pathogenesis, it is generally believed that aberrant forms of IgA in blood circulation are prone to aggregate into poly-IgA complexes. If not cleared by the liver promptly, poly-IgA can deposit in the kidney mesangium.

The major histologic features are granular diffuse IgA-dominant immune deposits in intraglomerular mesangial regions, frequently associated with mesangial hypercellularity and matrix expansion. The IgA deposits mainly consist of polymeric IgA1 with variable levels of complement (C3). IgG co-deposition with IgA is less frequent and correlates with higher mesangial and endocapillary cellularity scores. Overall, the clinical trajectory varies for reasons that are unclear, with cases in East and South East Asia that tend to follow aggressive progression of the disease. Meanwhile, renal biopsies of healthy allograft donors and non-selected autopsy series showed between 3% and 24.5% positive rates of mesangial IgAN-like deposition, further indicating the clinical and histologic diversity associated with glomerular IgA deposits.

Lab animals such as mice and rats do not spontaneously develop IgAN. Currently there is no robust animal or in vivo model of IgA nephropathy. Despite the fact that mouse IgA has different molecular features from human IgA, there are spontaneous and induced models of IgA deposition in the kidney. These include genetic ddY strains of mice with spontaneously developed IgA deposits and glomerular injury; dietary gluten- or vomitoxin-induced high serum IgA levels with glomerular deposits; autoimmune models of Bcl-2, LIGHT or BAFF transgenic mice with IgA overproduction; and transgenic expression of human IgA receptor FcαR1/CD89 (sCD89) together with human IgA1. These animal models usually present high baseline IgA levels in blood and to some extent resemble the human disease. However, they often have unpredictable onset of glomerular deposits with or without IgAN-like renal injury.

Without a robust model, it is particularly difficult to design a drug screening platform and to find therapeutic solutions to the disease. It has been reported that poly-IgA extracted from IgAN patients, if injected in a large quantity to mice, can cause renal deposition. Due to the variability in these studies from patient to patient as IgA donors, and a lack of molecular characterization of poly-IgA, these animal models of IgAN are not considered robust enough to be used in therapeutic drug screening.

Therefore, understanding the contributing factors to IgAN glomerular damage will be the key for developing new prognostic tools as well as disease-specific treatments, which are currently lacking. Mounting evidence suggests the O-glycosylation states of a "hinge" sequence between $C_H1$/Cα1 and $C_H2$/Cα2 domains of IgA1 heavy chain directly correlate with incidences of glomerular IgA deposits. Poorly galactosylated IgA1 is prone to self-aggregation and aberrant glycoforms of the hinge may also elicit antigenicity that promotes the formation of IgA-IgG autoimmune complexes. It should also be noted that the serine and threonine-rich (O-linked glycosylation sites) hinge sequence of IgA1 is only found in higher primates that include the great apes and humans. Since the critical hinge sequence that carries the O-glycans is absent in experimental animals, the study of IgAN with animal models has been challenging.

SUMMARY

Here, a different approach to specifically construct a recombinant IgA analog that can be artificially induced for multimerization at high efficiency. This synthetic poly-IgA, following its injection in rats, not only readily deposited in the glomerular mesangium, but also induced renal and systemic responses towards its clearance. This model is useful to study the dynamics of polymeric IgA deposition as well as clearance in the kidney to better understand IgAN pathogenesis and progression.

Herein described is a new recombinant IgA Fc fragment (rIgA) with a biotin tag that, following induction with streptavidin, forms high-order oligomers resembling poly-IgA. Injection with rat rIgA in polymeric form caused prominent renal glomerular mesangial deposition of rIgA, reminiscent of IgAN pathology in patients. Thus, this rat model of IgAN pathology is able to provide screening and evaluation of therapeutic drugs for IgAN, and ability to evaluate or assess diagnostic tests. The recombinant poly-IgA Fc can be easily standardized as an injection reagent to form kidney mesangium deposition in an animal to create an in vivo animal model.

In some aspects, a method for producing an IgA nephropathy animal model is described herein. The method may include providing a polymeric complex of unglycosylated IgA oligomeric fragments; and administering to an animal the polymeric complex of unglycosylated IgA fragments for a specified period of time. In this manner, the treatment induces in the animal kidney glomerulus mesangial deposition of the polymeric complex of unglycosylated IgA fragments. The deposition also induces renal and systemic responses toward clearance of the polymeric complex from the kidney. Both the deposition of the polymeric complex in the kidney glomerulus and the responses induced to clear the complex lead to an animal model of IgA nephropathy. The animal model is further useful for analysis of therapeutics and diagnostics intended for treatment or diagnosis of an IgA nephropathy.

In some aspects of the invention, a polymeric complex of unglycosylated IgA oligomeric fragments is provided. This polymeric complex is characterized by being homo-oligomeric, that is generated from multiple units that are similar or identical. In some aspects the complex is composed of IgA oligomeric fragments are IgA Fc oligomers. In some aspects, the complex is formed because each IgA oligomer of the complex comprises a biotin moiety and the polymeric complex resulting from the addition of streptavidin to a mixture of biotinylated IgA oligomeric fragments.

BRIEF DESCRIPTIONS OF DRAWINGS

Figure 1E:
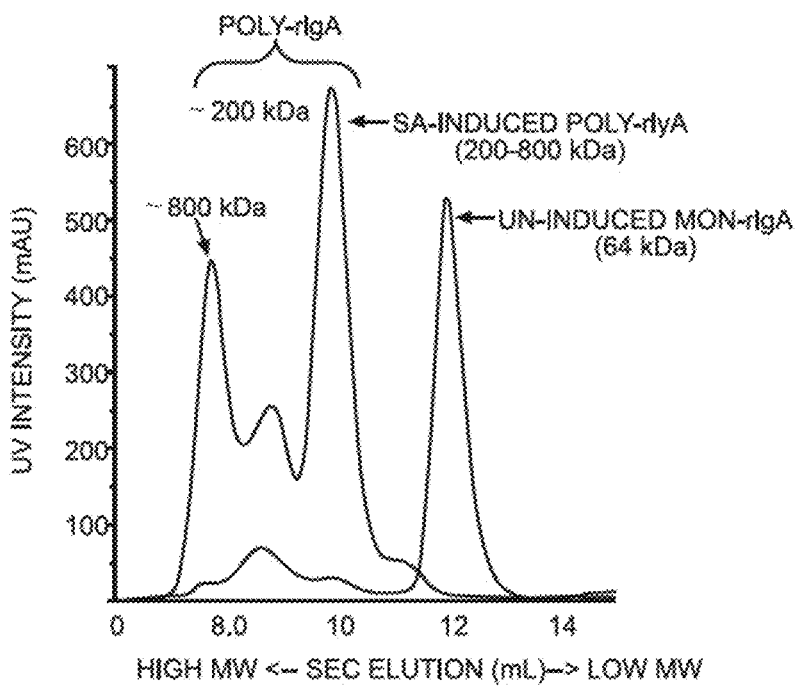

FIG. 1A-E represents construction of AviTag-IgA fusion protein and induction of multimerization by streptavidin according to one aspect of the invention. FIG. 1A: Immunoglobulin IgA heavy chain schematic. FIG. 1B: Recombinant Fc of rat IgA (rIgA) with an N-terminus AviTag that was subsequently biotinylated schematic according to one aspect of the invention. FIG. 1C-D: Gel electrophoresis and Western blotting indicating stable poly-rIgA formation. FIG. 1E: a graph indicating size-exclusion chromatography (SEC) elution.

Figure 2A:
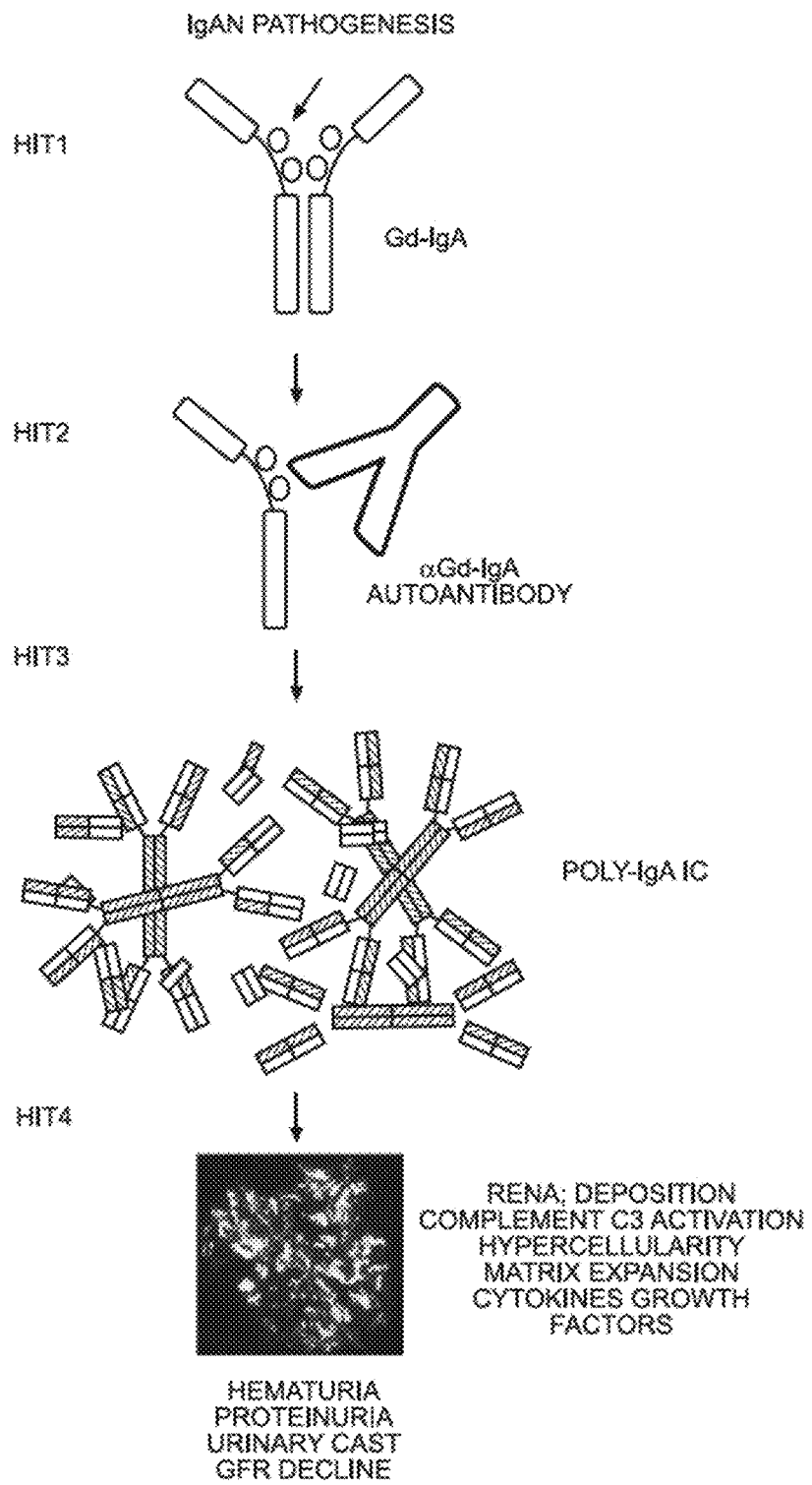
Figure 2B:
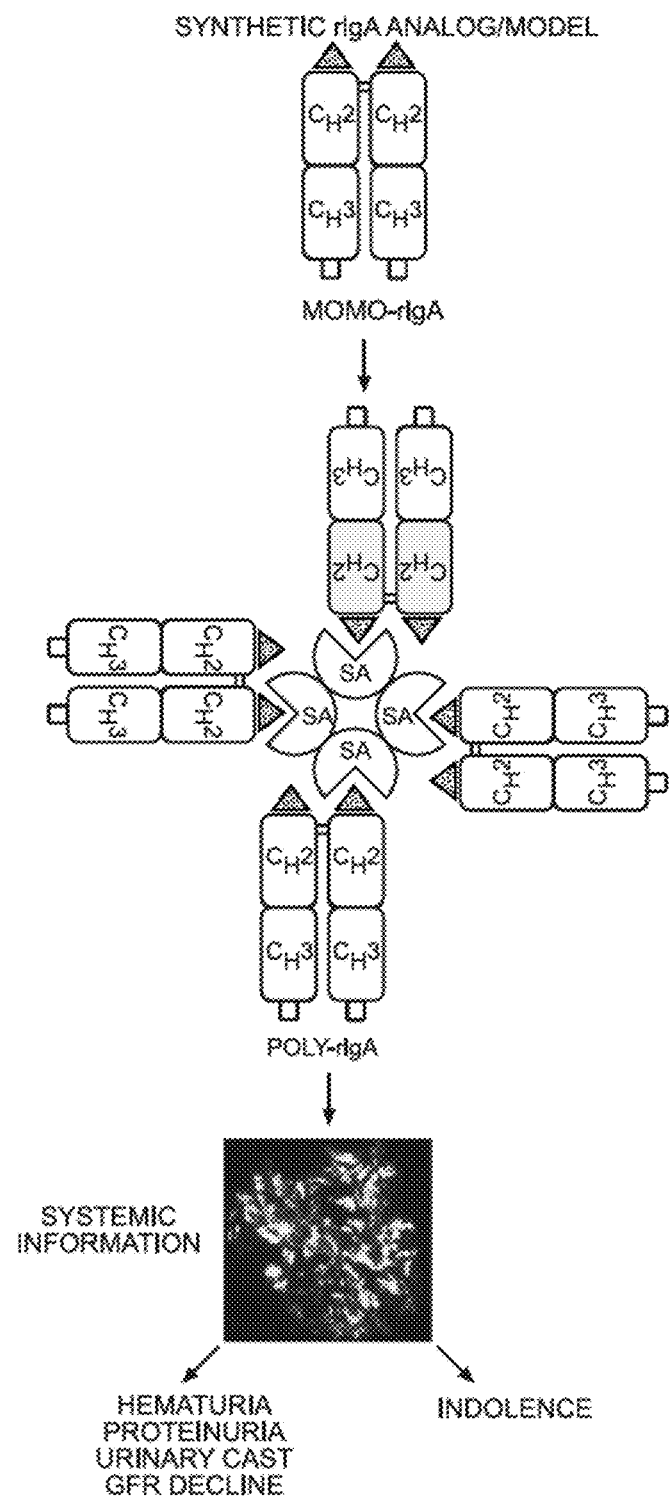

FIG. 2A-B schematic comparison between naturally formed poly-IgA 1 (FIG. 2A) and IgAN and synthetic poly-rIgA analog (FIG. 2B) according to one aspect of the invention.

Figure 3A:
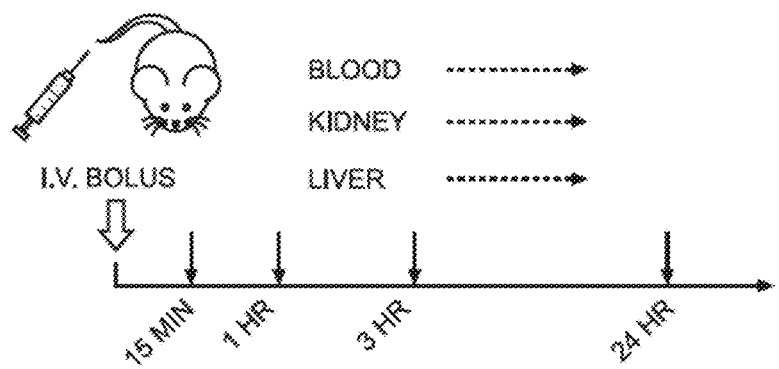
Figure 3B:
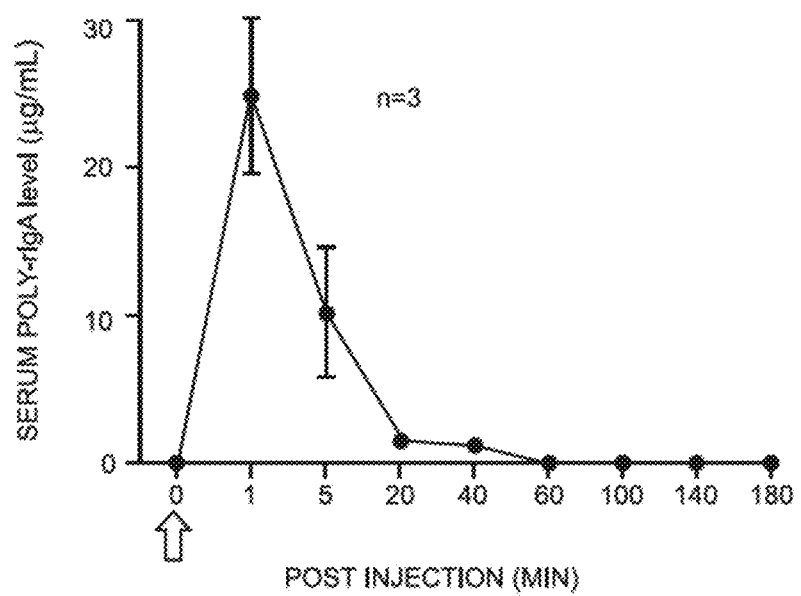

FIG. 3A-H represents systemic and targeted deposition and clearance of poly-IgA in rats after single dose rIgA injection according to one aspect of the invention. FIG. 3A, a schematic according to one aspect of the invention for bolus i.v. injection of poly-rIgA (open arrow), or mono-rIgA control and samples of blood, kidney and liver were collected (arrowheads) and levels of rIgA in the specimens were detected using anti-IgA antibody (broken arrows). FIG. 3B. a graph of the poly-rIgA contents measured by ELISA. FIG. 3C-F: immunofluorescence staining of kidneys and liver harvested at different timepoints according to one aspect of the invention (Scale bars: 50 μm).

FIGS. 4A-D immunofluorescence staining of kidneys (FIGS. 4A-C) and (FIG. 4D) liver harvested at different timepoints according to one aspect of the invention (Scale bars: 50 μm) demonstrating injection of mono-rIgA in rats did not form renal deposits according to one aspect of the invention.

Figure 5:
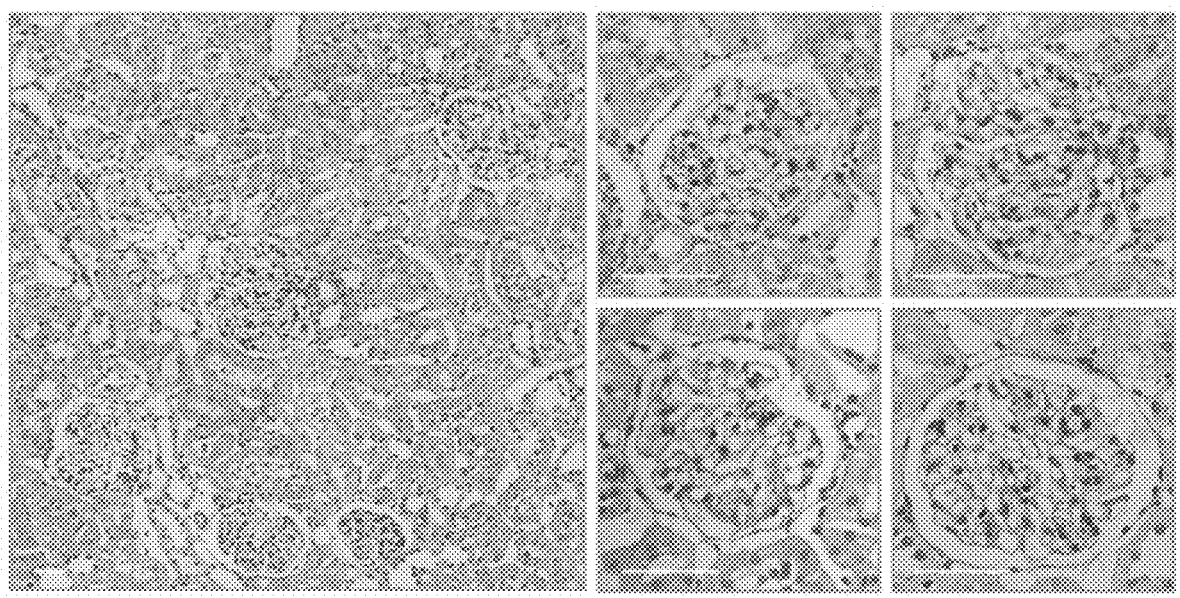

FIG. 5 represents normal renal histology following single dose of poly-rIgA injection according to one aspect of the invention. Scale bar: 50 μm.

Figure 6A:
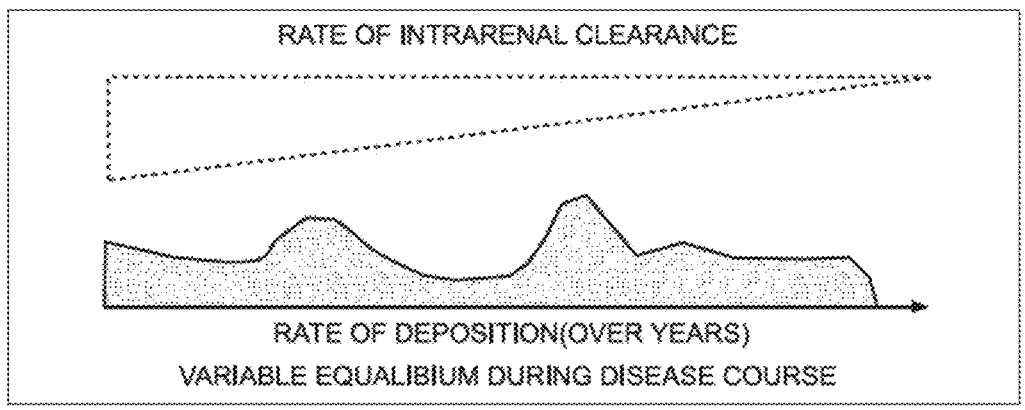
Figure 6B:
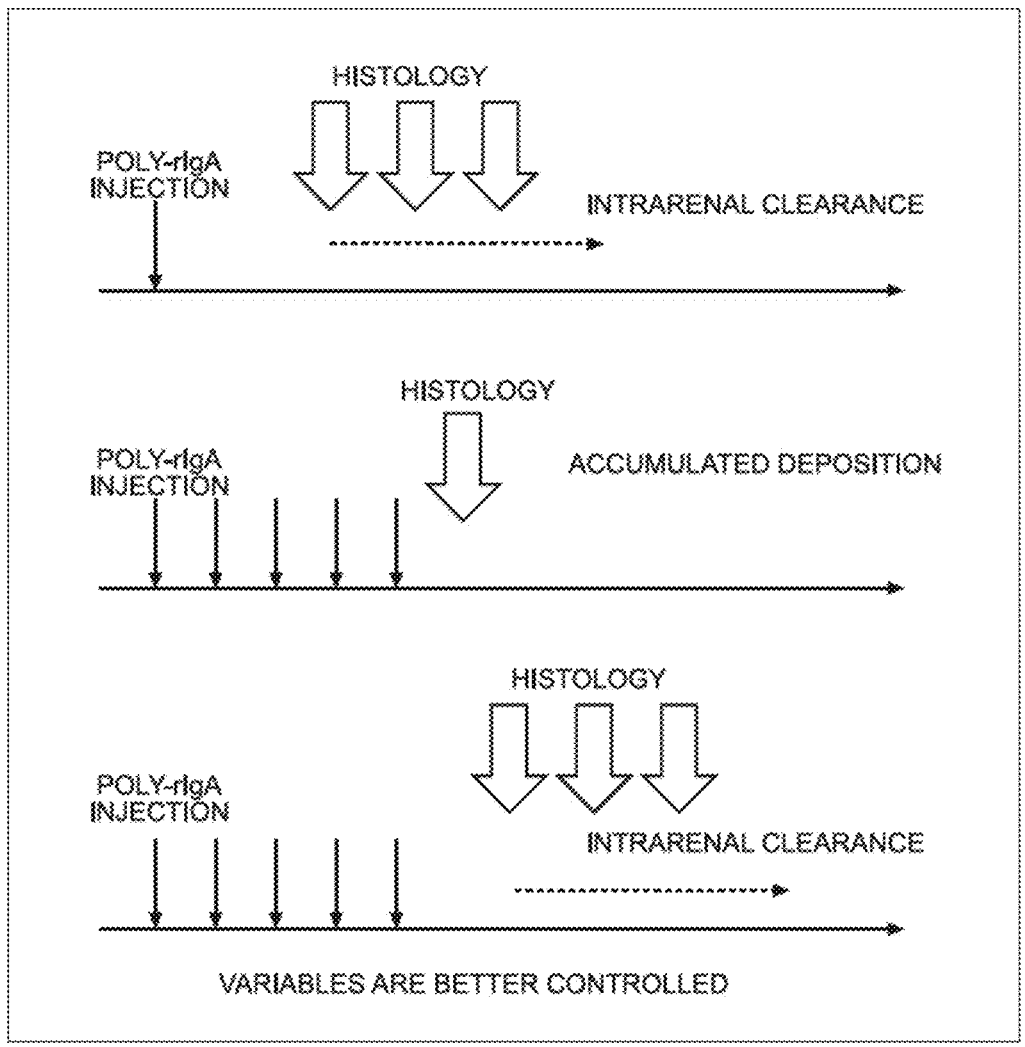

FIG. 6A-B demonstrate schematics of mesangial IgA deposits during the years-long disease course of IgAN (FIG. 6A) versus short poly-rIgA injection model (FIG. 6B) according to one aspect of the invention.

Figure 7A:
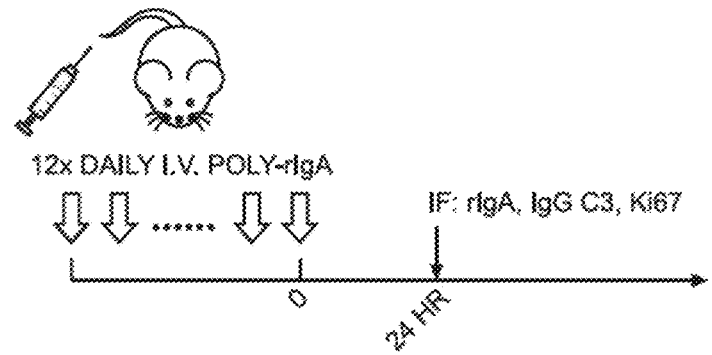

FIG. 7A-F represents analysis of consecutive daily injections of poly-IgA induced strong and long-lasting IgA deposits in glomerular mesangium according to one aspect of the invention. FIG. 7A represents a schematic according to one aspect of the invention for consecutive daily injections of poly-IgA and FIG. 7B-F represent immunofluorescence (IF) staining of rIgA, IgG deposits in the kidney, complement C3 and cell proliferation marker Ki67. Scale bars: 50 μm.

Figure 8A:
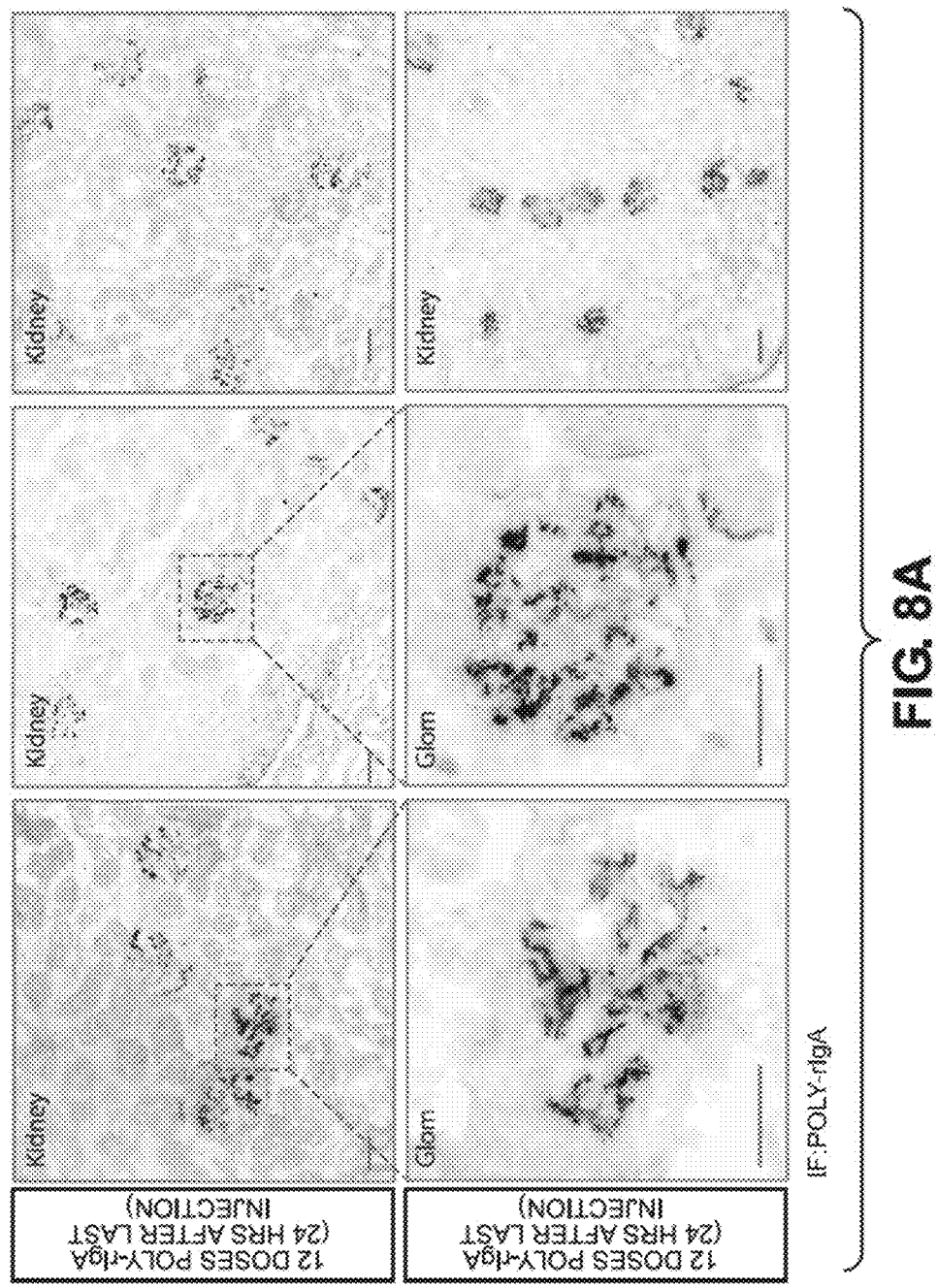
Figure 8B:
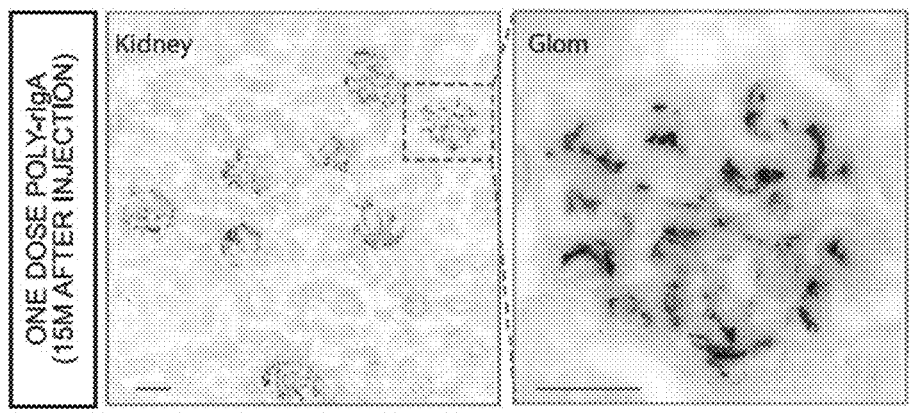

FIG. 8A-B: Immunofluorescence staining of poly-rIgA deposits in the kidney according to one aspect of the invention. FIG. 8A, after 12 consecutive doses of poly-rIgA injection. Insets showing mesangial and endo-capillary deposits and FIG. 8B, renal poly-rIgA deposition following single bolus injection.

Figure 9:
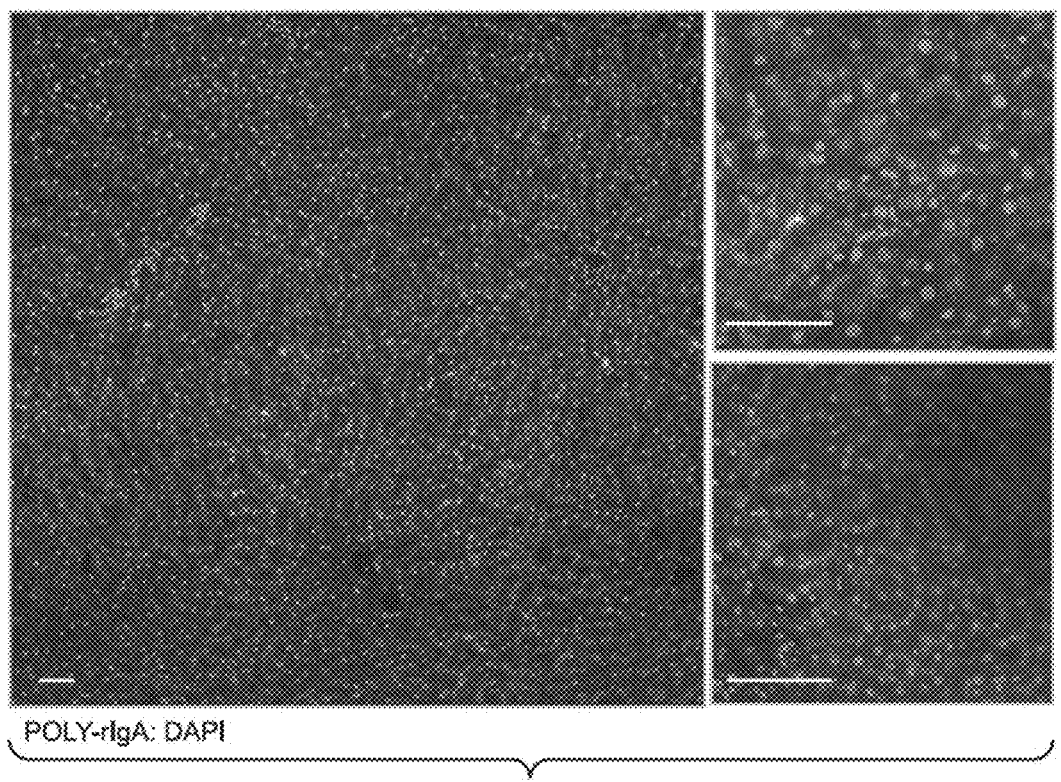

FIG. 9: Immunofluorescence staining demonstrating trace rIgA in the liver after twenty-four hours following twelve consecutive doses of poly-rIgA injection according to one aspect of the invention. Scale bars: 50 μm.

Figure 10A:
Figure 10B:
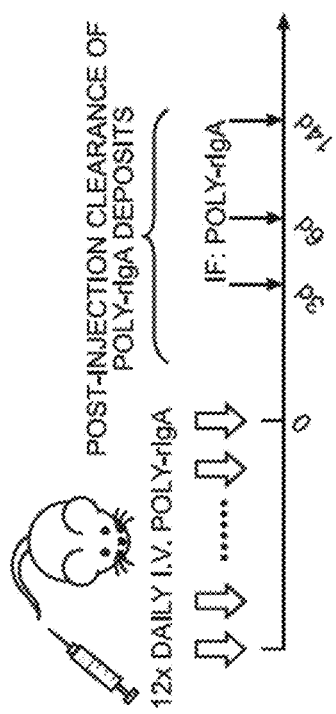
Figure 10C:
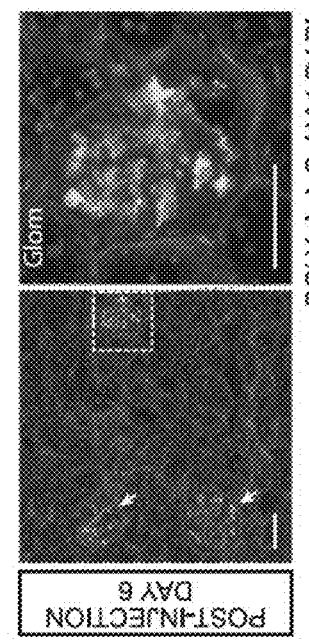
Figure 10D:
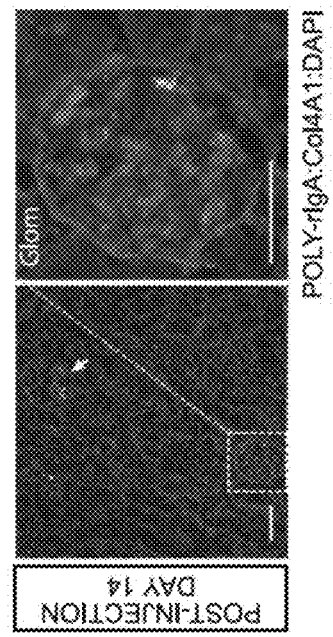

FIG. 10A-D: FIG. 10A represents a schematic according to one aspect of the invention and FIG. 10B-D represent immunofluorescence (IF) staining of poly-rIgA (Scale bars: 50 μm).

Figure 11:
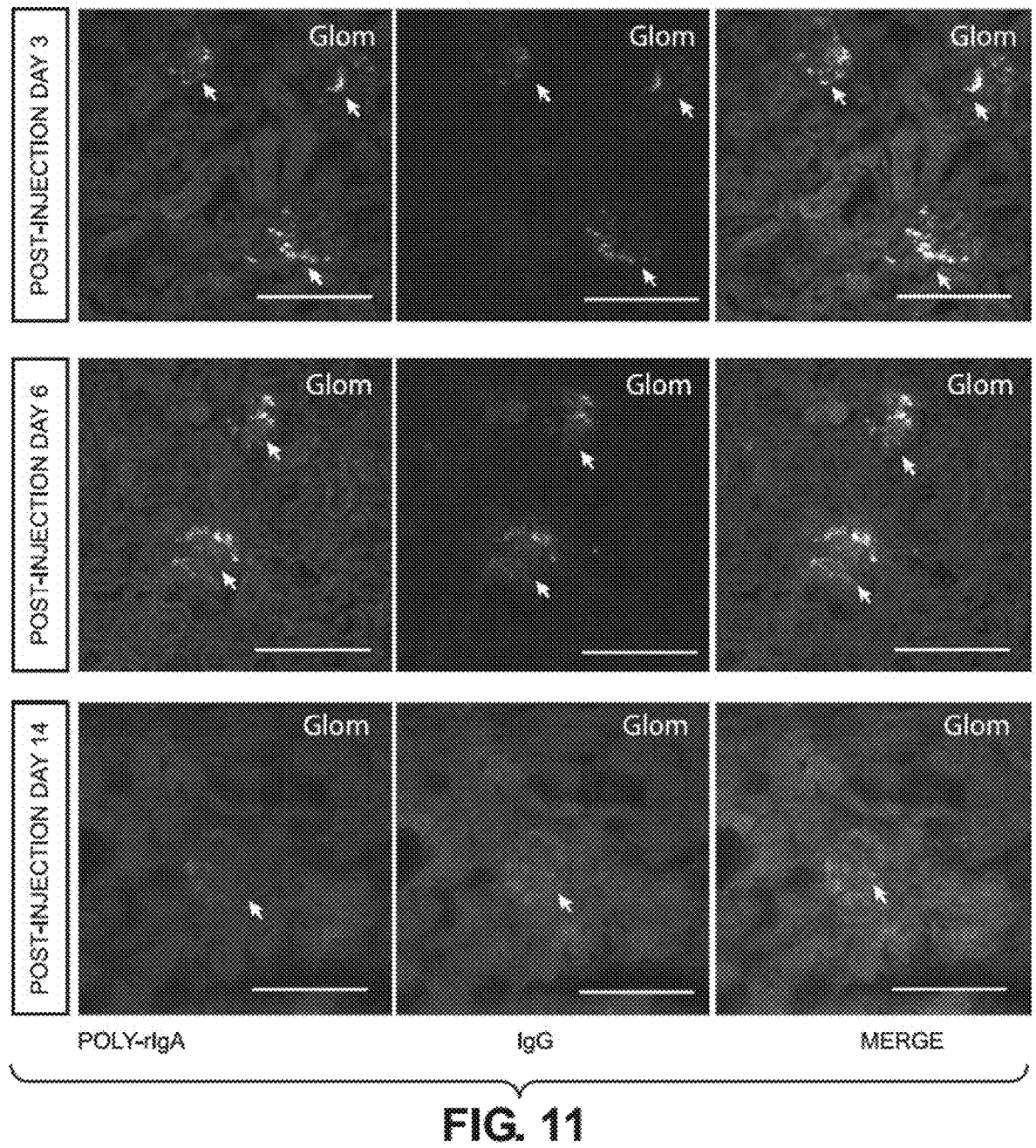

FIG. 11 represents time-dependent clearance of IgG co-deposition in rat kidney according to one aspect of the invention. Following twelve consecutive daily dosages of poly-rIgA, the rats were allowed to recover for three, six or fourteen days. On day three and day six, poly-rIgA and IgG co-deposits were visible in the glomerulus (arrows). By day fourteen, both poly-rIgA and IgG staining had disappeared (Scale bar: 5 μm).

Figure 12A:
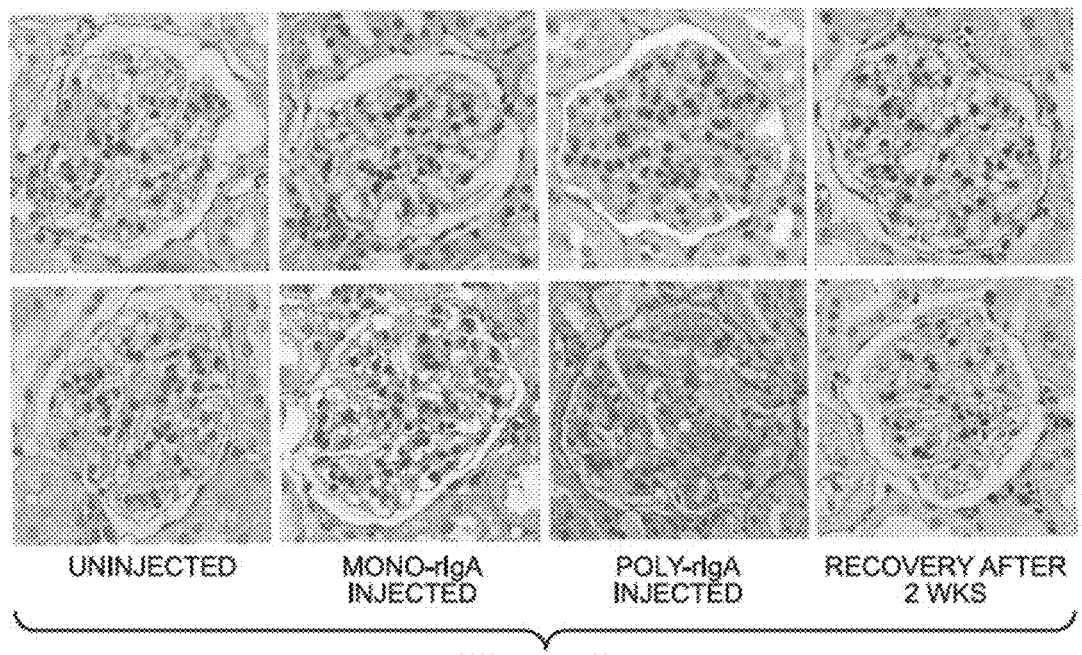
Figure 12B:
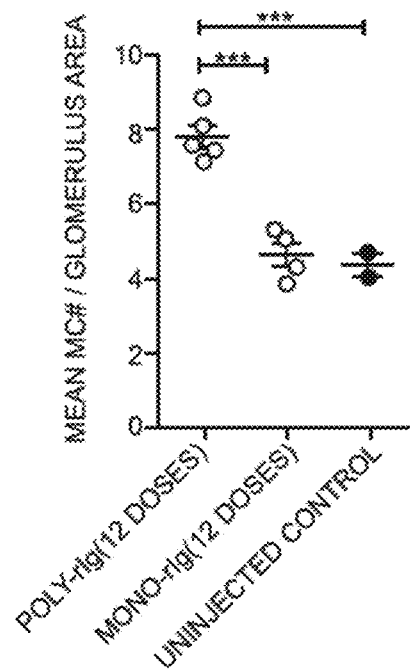

FIG. 12A-B represents histologic glomerulus changes according to one aspect of the invention. FIG. 12A: Periodic acid-Schiff (PAS) staining of rats kidney sections were performed to detect histologic changes to the glomerulus following no treatment, mono-rIgA injection for twelve days, poly-rIgA injection for twelve days, or poly-rIgA injection for twelve days and recovery for additional fourteen days. For each condition, two representative examples of glomerulus were shown (top and bottom). FIG. 12B: Statistical analysis of hypercellularity of the mesangium among poly-rIgA, mono-rIgA and uninjected groups. (triple asterisks: $p<0.001$).

Figure 13A:
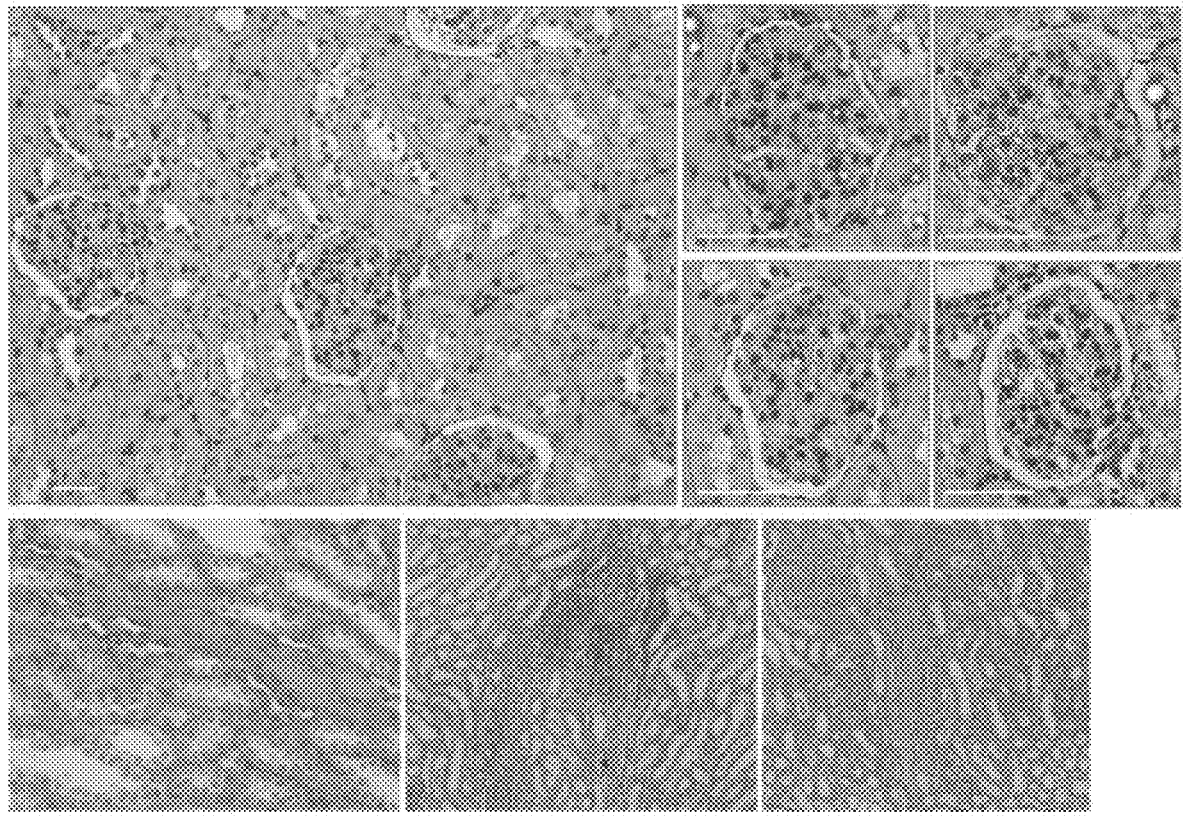
Figure 13B:
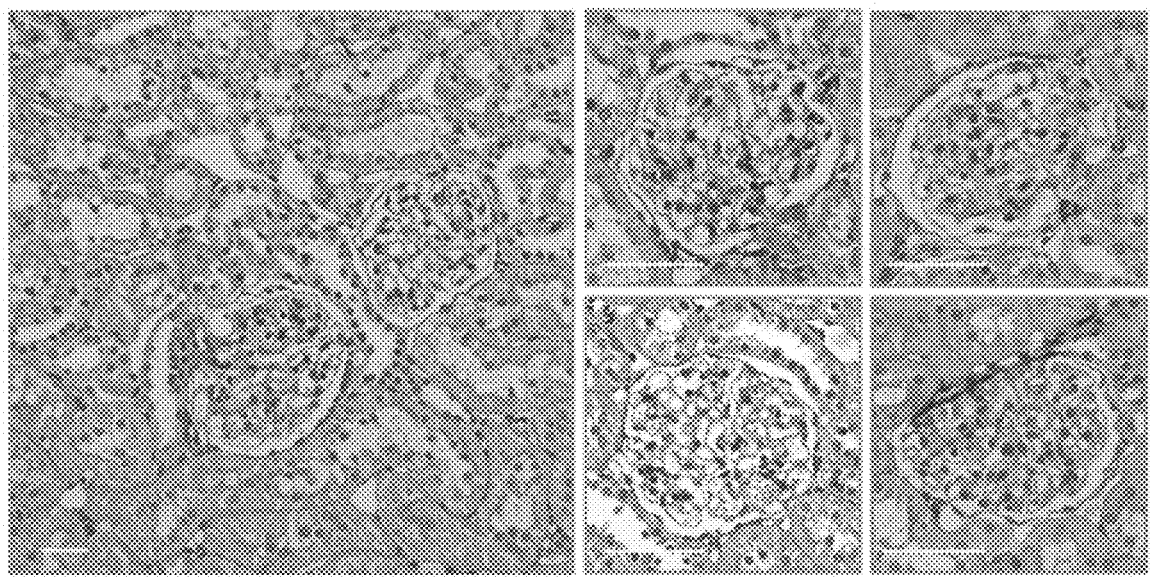

FIG. 13A-B represents renal histology features after twelve consecutive doses of poly-rIgA or mono-rIgA. Mesangial proliferation and matrix expansion were induced by poly-rIgA injections, two out of five rats had protein casts in the tubulointerstitium (FIG. 13A). Normal renal histology after twelve doses of mono-rIgA (FIG. 13B). Scale bar: 5 μm.

Figure 14A:
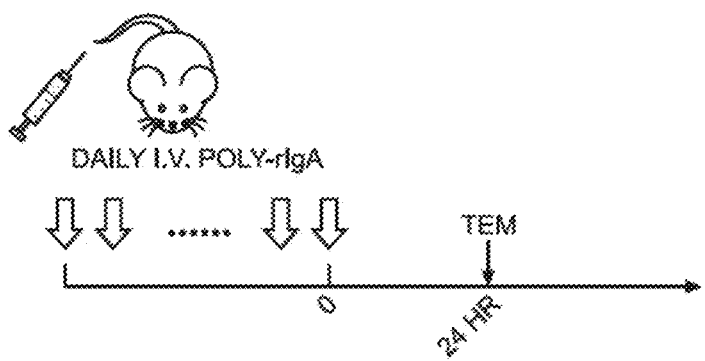
Figure 14B:
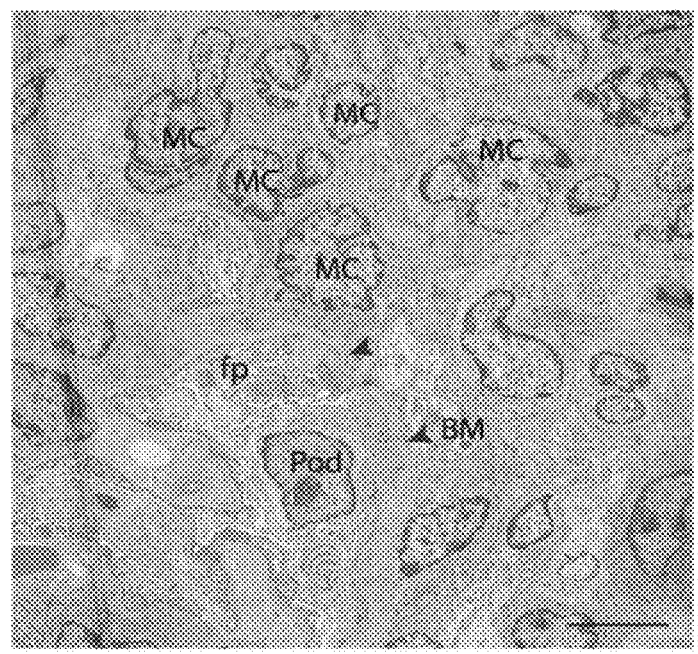
Figure 14C:
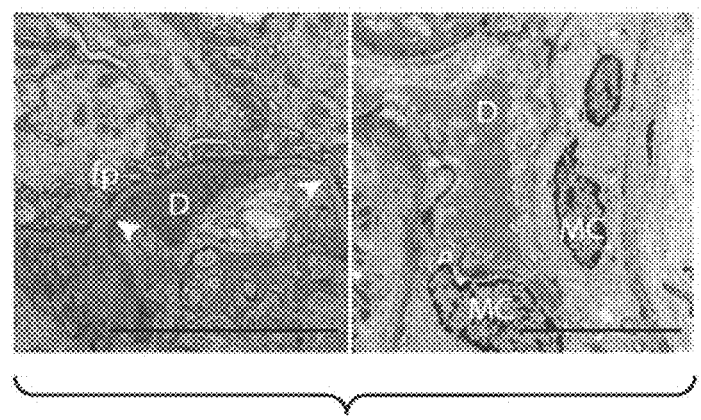

FIG. 14A-C represents electron microscopy shows deposits in subendothelial and mesangial regions according to one aspect of the invention. FIG. 14A: is a schematic indicating rats received 12 injections of poly-rIgA. Twenty-four hours following the last injection, the kidneys were collected for transmission electron microscopy (TEM). FIG. 14B: TEM revealed structures including mesangial cells (MC), glomerular basement membrane (GBM: pointed by arrowheads), podocyte (pod) and podocyte foot processes (fp). Scale bar: 5 μm. FIG. 14C: At higher magnification, electron dense deposits (denoted by letter D) could be seen on the endothelial side of the basement membrane (left panel) and the mesangium (right panel).

Figure 15B:
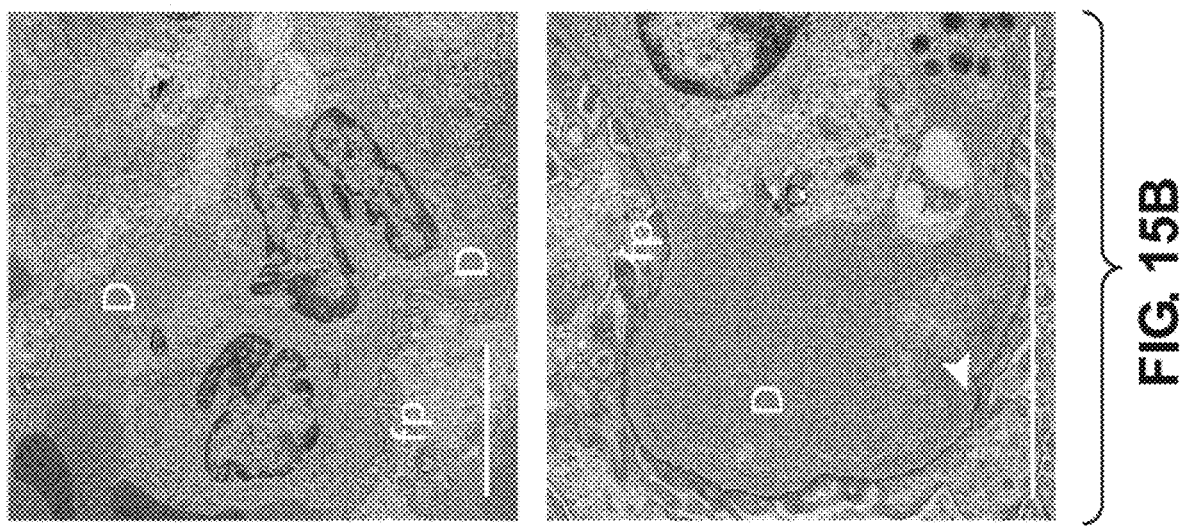
Figure 15A:
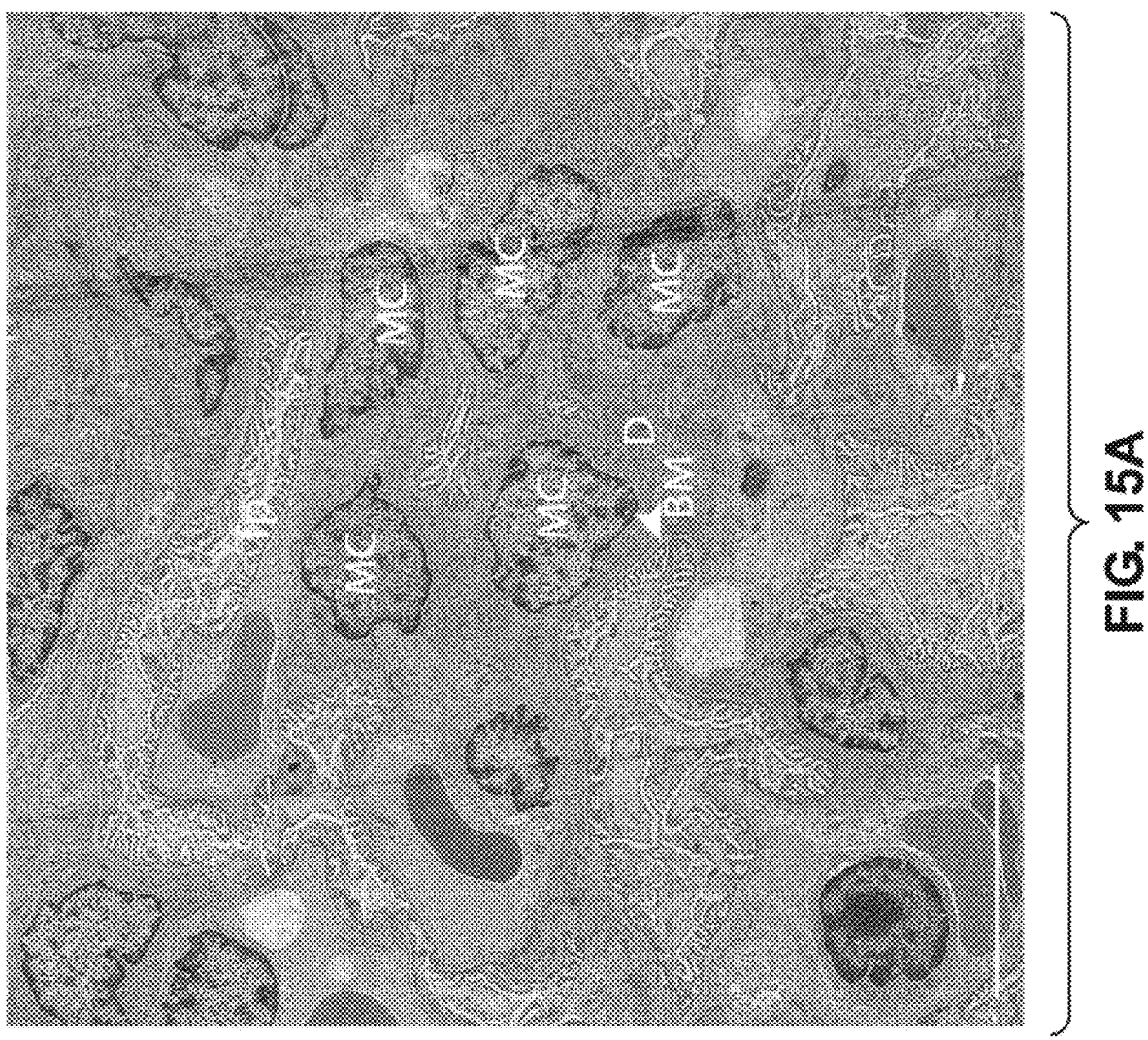

FIG. 15A-B represents electron microscopy of rat kidney after 12 injections of poly-rIgA according to one aspect of the invention. FIG. 15A: TEM overview of the glomerulus shows regions populated by mesangial cells (MC), density of irregular shape could be seen between mesangial cells. Basement membrane (BM: pointed by arrowheads), podocyte (pod) and foot processes (fp) appeared well preserved. Scale bar: 5 μm. FIG. 15B: At higher magnification, electron dense materials (denoted by letter D) could be seen on the endothelial side of the basement membrane (arrow). Foot processes (fp) appeared normal.

FIG. 16A-C represents proteinuria, urinary sediments, and serum creatinine analysis according to one aspect of the invention. FIG. 16A: PAS staining showed normal appearance of the tubule in uninjected and mono-rIgA-injected rats. FIG. 16B: Microscopic examination of the urinary sediments of the two albuminuric rats showed tissue clumps (arrowheads) that resembled urinary cases in patients. In addition, red blood cells (RBC) were visible (arrows), either in isolation or in association with the cast structures. FIG. 16C: Urinalysis by SDS PAGE.

Figure 17A:
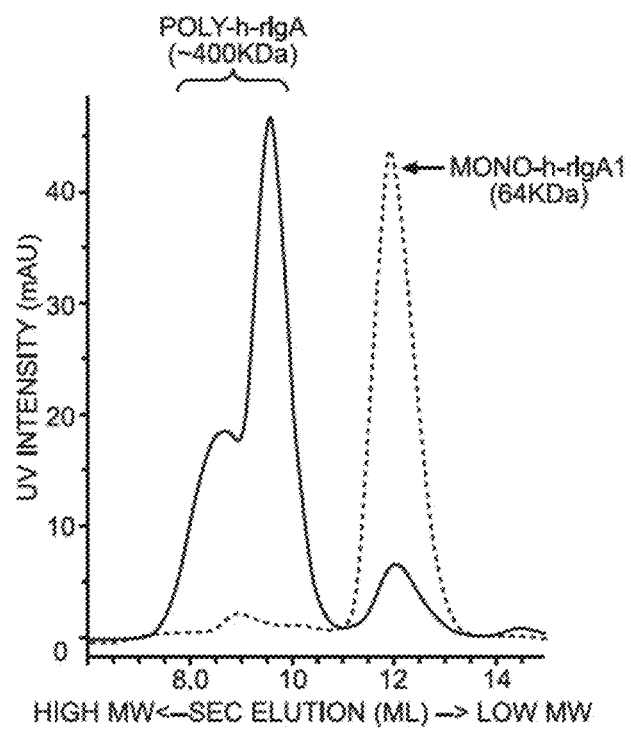
Figures 17B, 17C:
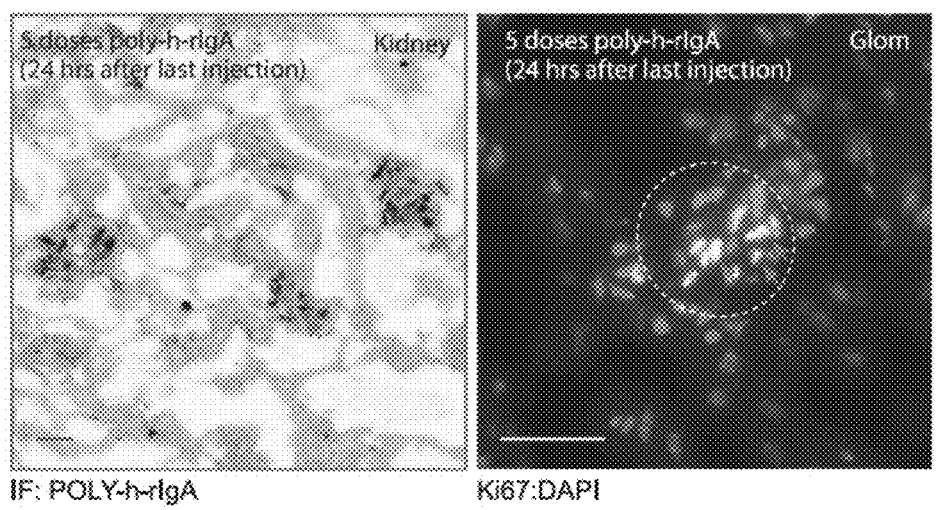

FIG. 17A-C represents human-derived poly-h-rIgA caused glomerulus deposition in mice according to one aspect of the invention. FIG. 17A size exclusion chromatography of recombinant IgA Fc produced in HEK293 cells. Injection of this poly-h-rIgA in mouse for five consecutive days resulted in renal deposition detected by anti-IgA staining (FIG. 17B). The staining was concentrated in glomerulus areas (arrows). In addition, staining of the kidney sections with Ki67 (FIG. 17C) showed positive nuclei (arrows) within the glomerulus (circle), indicating active cell proliferation.

Figure 18A:
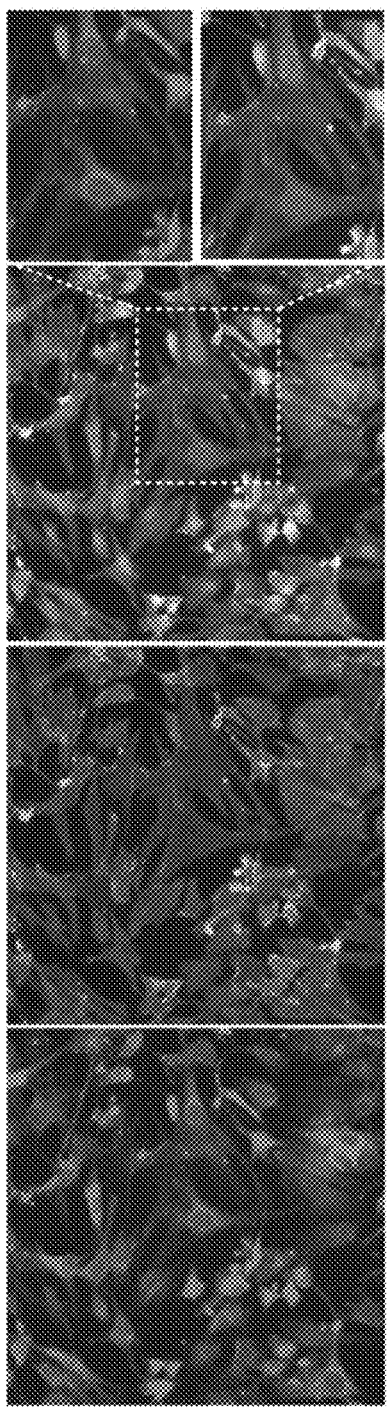
Figure 18B:
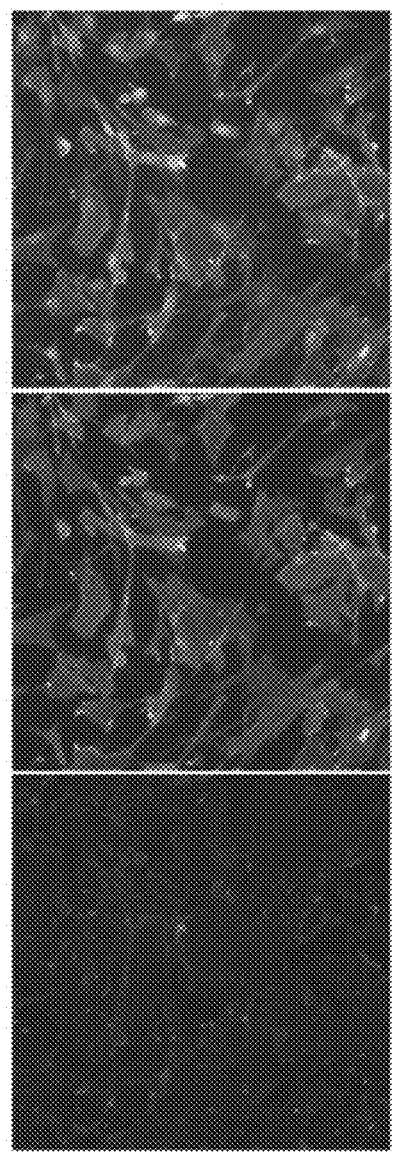
Figure 18C:
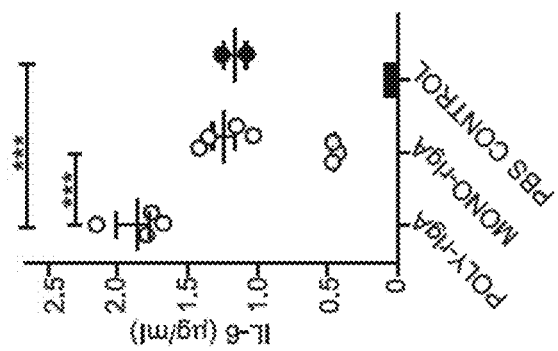

FIG. 18A-C represents poly-IgA binding renal mesangial cells in culture according to one aspect of the invention. Human glomerular mesangial cells were cultured in dishes. Human biotin-h-rIgA either in the SA-induced polymeric (FIG. 18A) or uninduced monomeric (FIG. 18B) state was added to culture medium. Following washing to remove unbound h-rIgA, the cells were fixed and then probed for IgA contents. Phalloidin staining for Actin and DAPI for nucleus were the counterstains. In FIG. 18C, following coculture of the cells with either poly- or mono-h-rIgA for overnight, the culture medium was harvested for detection of IL-6 by ELISA (y-axis).

Figure 19A:
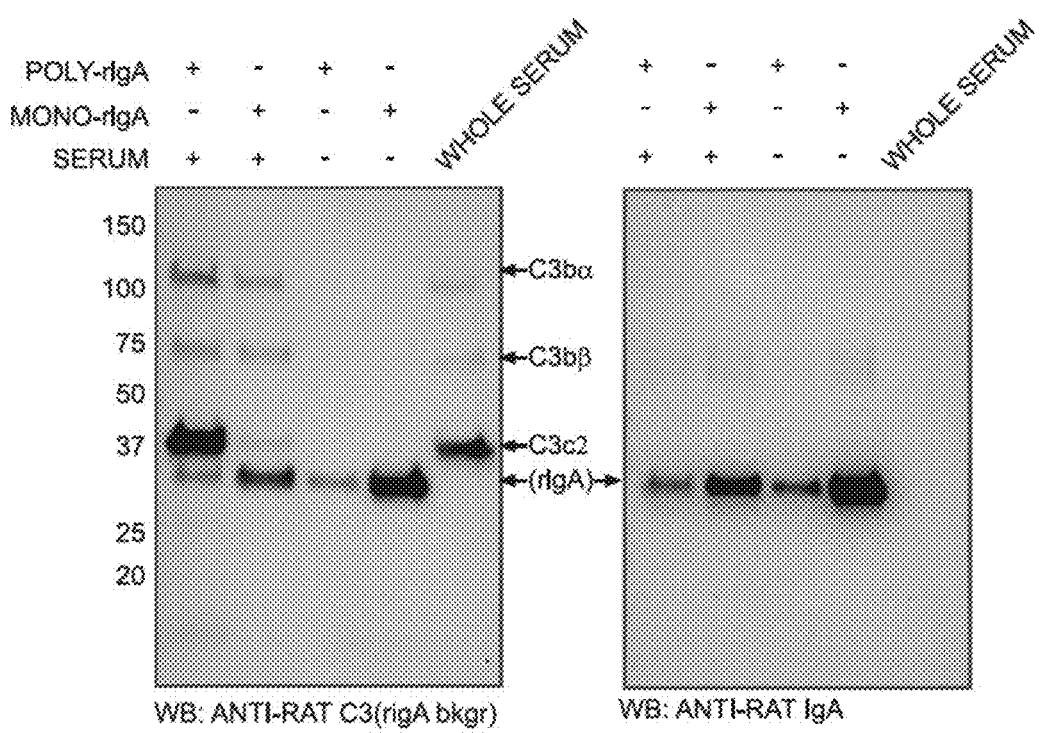
Figure 19B:
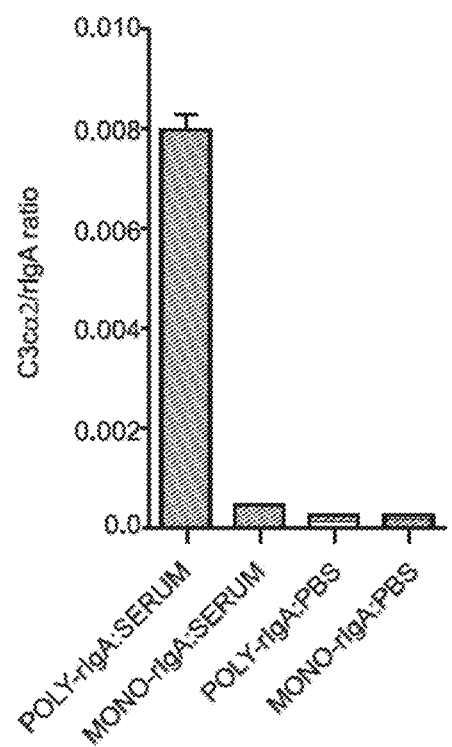
Figure 19C:
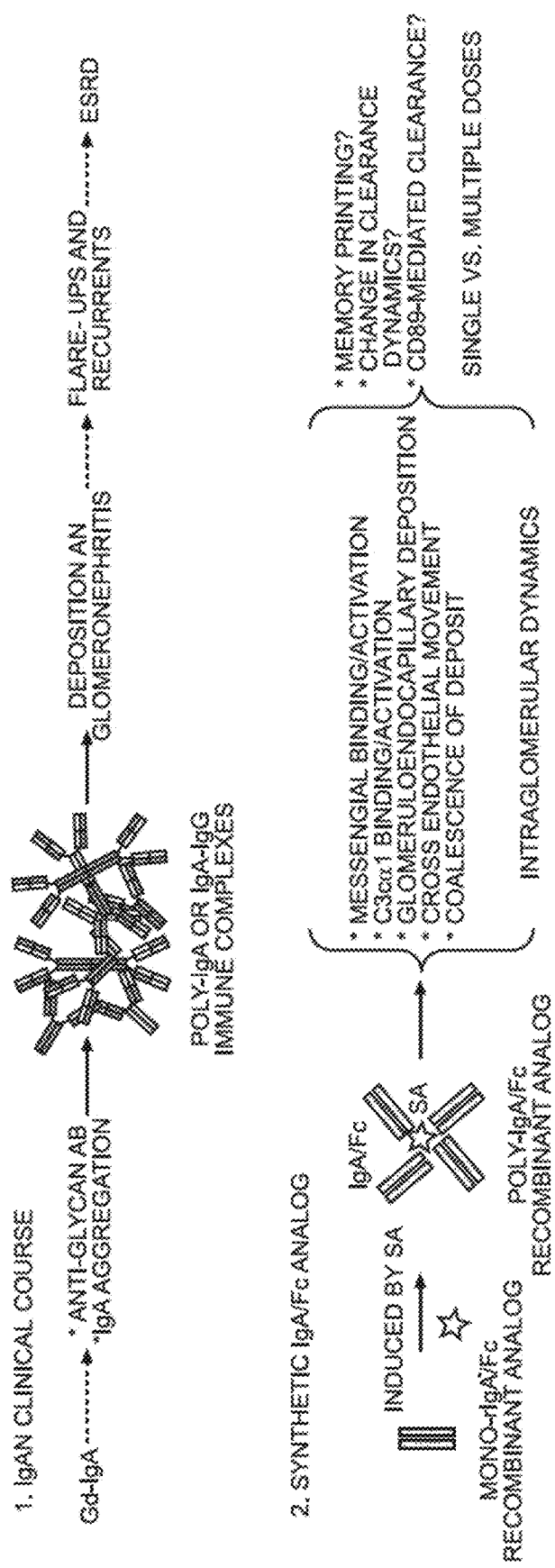

FIG. 19A-C represents activation complement in vitro by poly-rIgA according to one aspect of the invention. FIG. 19A: Rat poly-rIgA and mono-rIgA were separately incubated with freshly harvested rat serum. These 6×His-tagged rIgA proteins were then immobilized by Ni'-NTA beads. Following elution with sample buffer, all proteins were resolved by SDS PAGE, which was subsequently examined by Western blotting (WB) with either anti-C3 or anti-IgA antibody (left and right panels, respectively). Several C3 bands were visible that corresponding to C3bα, C3bβ and C3cα2. FIG. 19B: C3cα2 to rIgA ratios were calculated, showing C3cα2 association with poly-rIgA. FIG. 19C: A schematic model for the pathogenesis of poly-IgA immune complexes in IgAN as revealed by synthetic poly-rIgA analog.

FIG. 20A-C represent a schematic for a variety of multimeric states of poly-rIgA induced by streptavidin according to aspects of the invention.

Figure 21:
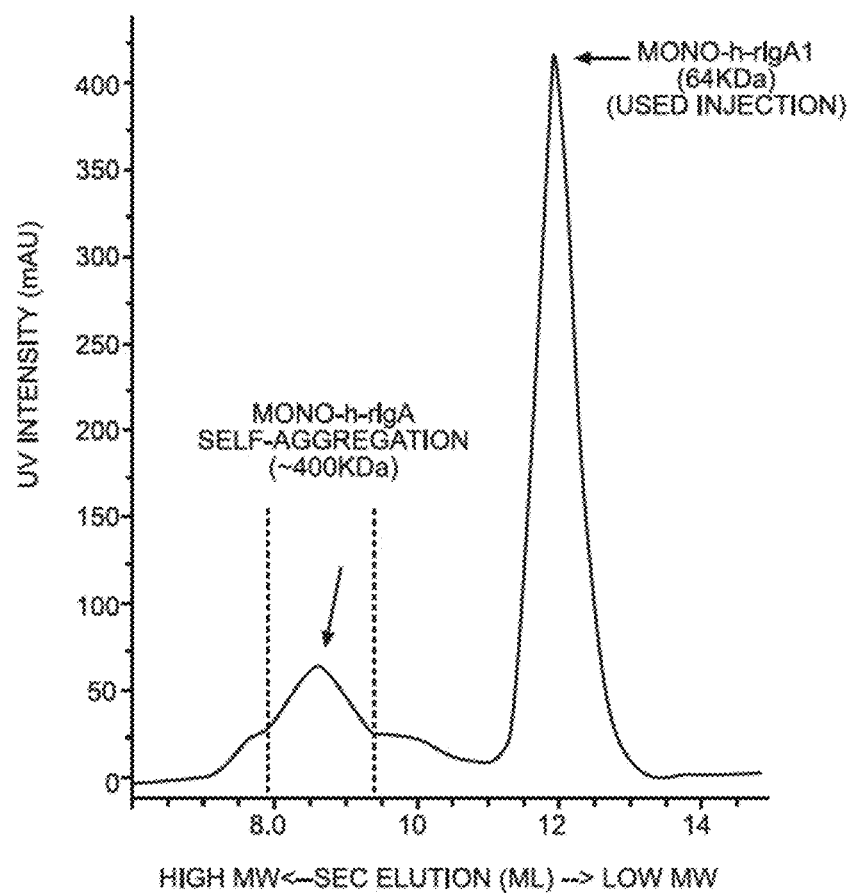

FIG. 21 represents size exclusion chromatography of recombinant mono-rIgA according to one aspect of the invention indicating the sample may contain a small fraction of polymers from self-aggregation.

DETAILED DESCRIPTION

IgA immune complexes in circulation are the primary source of renal deposits in IgA nephropathy (IgAN). IgA1 with poorly glycosylated hinge region tends to self-aggregate and form IgG-IgA autoimmune complexes. Most mammals, except for higher primates, lack this hinge segment and this has been a major obstacle for establishing robust animal models of IgAN. A synthetic approach to produce a recombinant fusion between IgA Fc (rIgA) and a biotin tag, which was subsequently induced with streptavidin to form high-order oligomers in mimicking poly-IgA. Following injection in Wistar rats, this synthetic poly-rIgA analog formed renal deposits exclusively in the glomerulus. The deposits were mostly cleared in three hours. However, repeated daily injections for twelve days caused long-lasting glomerular deposition with the presence of IgG and complement C3 co-deposition, in association with mesangial cell proliferation and matrix expansion with variable degrees of albuminuria and hematuria that phenocopied IgAN. In contrast, monomeric rIgA control did not form renal deposits, suggesting simple configurations of poly-IgA complexes are sufficient for glomerular deposition, possibly attributable to poly-IgA Fc's high avidity effect. Ex vivo, poly-rIgA bound cultured mesangial cells and elicited cytokine production of the cells, in addition to activating plasma C3 that is consistent with the actions of IgA immune complexes in IgAN pathogenesis. Unlike chronic models of IgAN, the synthetic model allowed to follow the kinetics between the balance of renal deposition versus clearance, which revealed priming effects of existing deposits in promoting stronger and longer-lasting IgA deposition to cause renal damage.

As will now be described in detail, herein provided is a method for producing an in vivo IgA nephropathy animal model includes providing a recombinant IgA oligomer, treating the animal with the recombinant IgA oligomer so that the treatment induces kidney glomerulus mesangial deposition in the animal thereby producing an animal model of IgA nephropathy.

A method for producing an IgA nephropathy animal model is described herein. The method may include providing a polymeric complex of unglycosylated IgA oligomeric fragments; and administering to an animal the polymeric complex of unglycosylated IgA fragments for a specified period of time. In this manner, the treatment induces in the animal kidney glomerulus mesangial deposition of the polymeric complex of unglycosylated IgA fragments. The deposition also induces renal and systemic responses toward clearance of the polymeric complex from the kidney. Both the deposition of the polymeric complex in the kidney glomerulus and the responses induced to clear the complex lead to an animal model of IgA nephropathy.

Referring to the polymeric complex of unglycosylated IgA oligomeric fragments specifically, it is noted that the complex is formed from more than one oligomer, that is more than one polymeric unit. The IgA oligomeric fragments provided do not contain any type of sugar covalently bound to the protein that represents the IgA oligomeric fragment. The term fragment is intended to refer to any IgA protein sequence or protein subsequence. In some aspects, this subsequence may refer to the section of the IgA protein commonly known as an Fc fragment, portion, or section. However, it is appreciated that a polymeric complex may be formed from any subsequence of an IgA protein. The phrase oligomer refers to single unit representing a subsequence that has the activity of binding commonly associated with an Fc. The oligomer itself may represent a single protein strand or chain or two protein strands or chains as commonly found in an antibody. In some aspects, the polymeric complex is formed of identical IgA oligomeric fragments making the polymeric complex homo-oligomeric. In some aspects the polymeric complex is about 200 kDa to about 800 kDa in size. In some aspects, each of the IgA oligomeric fragments comprises a biotin moiety and the polymeric complex is formed by the addition of streptavidin to a mixture of biotinylated IgA oligomeric fragments. Though it is appreciated that any known methods of tagging and subsequently binding to that tag that are know in the art are applicable to formation of polymeric complexes according to the invention. In some aspects, the polymeric complex comprises two, three, four or seven IgA oligomeric fragments. Though it is appreciated that larger complexes may also be formed.

To form the animal model is formed by intravenous injection of the polymeric complex of unglycosylated IgA fragments. In some aspects the polymeric complex of unglycosylated IgA fragments is administered to the animal in a single injection and in some aspects, the polymeric complex of unglycosylated IgA fragments is administered to the animal daily for one to twelve consecutive days.

It is important to note that in some aspects the animal model demonstrates histologic changes of the glomerulus such as mesangial hypercellularity, matrix expansion, narrowing of capillary loops that are indicating of an IgA nephropathy. In this way, the animal model according to some aspects of the invention is additionally useful for determining the efficacy of a therapeutic agent for IgA nephropathy. In some aspects, the method may include steps of treating an animal model with a therapeutic agent; and evaluating glomerulus mesangial deposition of the polymeric complex of unglycosylated IgA oligomeric fragments or histologic changes after treatment so as to determining the efficacy of the therapeutic agent.

In some aspects the method of generating an animal model for IgA nephropathy additional provides for determining the efficacy of a diagnostic method of IgA nephropathy in a subject. After applying a diagnostic method to the animal model, and evaluating IgA indicators such as glomerulus mesangial deposition of a polymeric complex of unglycosylated IgA oligomeric fragments or histologic changes in the animal one may obtain a correlation between the diagnostic method and IgA indicators. This process enables determination of the efficacy of the diagnostic method.

In some aspects, the animal model is a rodent. In some aspects, a method of inducing IgA nephropathy in a subject. The method would include steps of providing a polymeric complex of unglycosylated IgA oligomeric fragments; and administering to a subject the polymeric complex of unglycosylated IgA fragments for a specified period of time. The result of these method steps would be to induce in the subject histologic changes that are hallmarks of IgA nephropathy.

In some aspects of the invention, a polymeric complex of unglycosylated IgA oligomeric fragments is provided. This polymeric complex is characterized by being homo-oligomeric. In some aspects the complex is composed of IgA oligomeric fragments are IgA Fc oligomers. In some aspects, the complex is formed because each IgA oligomer of the complex comprises a biotin moiety and the polymeric complex resulting from the addition of streptavidin to a mixture of biotinylated IgA oligomeric fragments.

In some aspects, a recombinant IgA comprises a C-terminal avidin tag. The tag may be added to other locations within the IgA protein. The tag may be encoded by nucleotides that are added to a recombinantly expressed protein. The tag may be covalently or non-covalently added to an IgA at the protein level. In some cases, the recombinant IgA oligomer comprises about four biotinylated rIgA antibodies for each streptavidin molecule.

The animal model generated by the method of treatment of an animal with a recombinant IgA oligomer is useful for evaluation of diagnostic methods and therapeutic treatments of subjects that have, or are suspected of having IgA nephropathy or any disorder in which IgA aggregates are found to accumulate in the glomerulus, among other organs and tissues. These methods would include, for example, preparing an animal model, applying to the animal model a diagnostic method to be tested or a therapeutic agent to be tested for an appropriate amount of time. At some time after the diagnostic or therapeutic agent is administered, the efficacy of the diagnostic or therapeutic is evaluated by determining the amount of glomerular mesangial deposition of the recombinant IgA oligomer as compared to an animal model that did not received the diagnostic or therapeutic agent. The subject may be a human.

Definitions

IgA nephropathy is equivalent to IgAN. rIgA refers to the recombinant IgA of the invention. The phrase poly IgA refers to a complex comprising more than one IgA. This refers to both a process that occurs in the etiology of IgAN as well as the in vitro formation of a complex of more than one IgA. IgA refers to any protein defined as an immunoglobulin A or fragment thereof.

Unless otherwise specified, "a," "an," "the," "one or more of," and "at least one" are used interchangeably. The singular forms "a", "an," and "the" are inclusive of their plural forms.

The recitations of numerical ranges by endpoints include all numbers subsumed within that range (e.g., 0.5 to 5 includes 1, 1.5, 2, 2.75, 3, 3.80, 4, 5, etc.).

The term "about," when referring to a value or to an amount of mass, weight, time, volume, concentration, or percentage is meant to encompass variations of ±10% from the specified amount. The terms "comprising" and "including" are intended to be equivalent and open-ended. The phrase "consisting essentially of" means that the composition or method may include additional ingredients and/or steps, but only if the additional ingredients and/or steps do not materially alter the basic and novel characteristics of the claimed composition or method. The phrase "selected from the group consisting of" is meant to include mixtures of the listed group.

Moreover, the present disclosure also contemplates that in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

The meaning of abbreviations is as follows: "C" means Celsius or degrees Celsius, as is clear from its usage, "s" means second(s), "min" means minute(s), "h," "hr," or "hrs" means hour(s), "psi" means pounds per square inch, "nm" means nanometers, "d" means day(s), "µL" or "uL" or "ul" means microliter(s), "mL" means milliliter(s), "L" means liter(s), "mm" means millimeter(s), "nm" means nanometers, "mM" means millimolar, "µM" or "uM" means micromolar, "M" means molar, "mmol" means millimole(s), "µmol" or "uMol" means micromole(s)", "g" means gram(s), "µg" or "ug" means microgram(s) and "ng" means nanogram(s), "kDa" means kilodaltons, "g" means the gravitation constant, "bp" means base pair(s), "kbp" means kilobase pair(s), "% w/v" means weight/volume percent, "% v/v" means volume/volume percent

EXAMPLES

Certain embodiments are described below in the form of examples. While the embodiments are described in considerable detail, it is not the intention to restrict or in any way limit the scope of the appended claims to such detail, or to any particular embodiment.

Example 1: Construction of Recombinant IgA-Biotin Fusion for Oligomeric Induction with Streptavidin Serum IgA interacts with its cognate Fc receptor FcαR1/CD89 of the mononuclear phagocytes. The process plays a key role in the clearance of IgA immune complexes, particularly by the Kupffer cells in the liver acting on circulatory complexes, and possibly also by macrophages/monocytes to clear tissue deposits. As an initial step, the sequence of a protein from rat, which shares high degree of homology with the human sequence at the CD89 receptor is provided. Though of course, any sequence of an Fc IgA from any species is usable in the invention as described.

Referring to FIG. 1, FIG. 1A depicts a schematic of an immunoglobulin IgA heavy chain is comprised of variable domain $V_H$ and constant domains $C_H1$-3 in an N- to C-terminus order. $C_H2$ and $C_H3$ together are referred to as Fc segment that mediates immune reactions, including receptor binding and complement activation. The stars represent glycosylation sites. In human IgA1, the hinge region that connects $C_H1$ and $C_H2$ are heavily glycosylated. However, rat IgA lacks glycosylated hinge. In FIG. 1B, a recombinant Fc of rat IgA (rIgA) with an N-terminus AviTag that was subsequently biotinylated is constructed. In FIG. 1C, induction of this mono-rIgA analog with streptavidin resulted in stable poly-rIgA formation that mimics poly-IgA in IgAN. In FIG. 1D, recombinant rIgA was produced from *E. coli*, and high molecular weight poly-rIgA formation following streptavidin (SA) induction was shown by SDS PAGE and Western blotting (left and right panels, respectively). In FIG. 1E, under phosphate buffered saline condition at neutral pH, the molecular sizes of mono-rIgA and streptavidin-induced poly-rIgA were compared. Size-exclusion chromatography (SEC) elution sequence showed significant up(left)-shifting of poly-rIgA in molecule size from uninduced mono-rIgA counterpart, from 64 kDa to 200-800 kDa. There existed several species of poly-rIgA with distinct complex sizes (see also FIG. 20). There were also low levels of high molecular weight content of un-induced rIgA (see also FIG. 21).

Referring to FIG. 2, FIG. 2A depicts a schematic comparison between naturally formed poly-IgA1 in IgAN and synthetic poly-rIgA analog. In the 4 Hits hypothesis, aberrantly glycosylated Gd-IgA1 is the root cause of IgAN. It has an intrinsic tendency to form protein aggregates and may induce antiglycan IgG autoantibodies in forming IgA1-IgG complexes. These poly-IgA1 complexes ultimately deposit in the glomerulus, causing inflammation and renal damage. In FIG. 2B a constructed recombinant fusion between IgA Fc (CH2/CH3) and biotin. This rIgA analog can be induced to form high-order oligomers by adding streptavidin (SA). This poly-rIgA, not its uninduced mono-rIgA counterpart, formed glomerular deposits in the kidney that resembled many of the clinical manifestations of IgAN.

Rat has only one IgA gene, which lacks the equivalent of the hinge region in human IgA1 heavy chain. The C-terminal half of the heavy chain is referred to as the Fc segment that interacts with IgA receptors (FIG. 1A), including CD89, to potentiate cellular and complement responses. A Fc of rat IgA following a recombinant fusion strategy with an N-terminus AviTag was produced (FIG. 1B). Site-directed biotinylation of the AviTag was performed with BirA ligase (FIGS. 1B and 1D). Using streptavidin (SA) that exists as a tetramer it is possible to artificially induced oligomerization of Fc via a stable interaction between SA and biotin (FIGS. 1C and 1D). The molecular size of the rIgA oligomer was 200~800 KDa as estimated by size exclusion chromatography (SEC) (FIG. 1E). This synthetic complex of recombinant IgA (referred to as poly-rIgA) a mimetic of naturally formed polymeric IgA as seen in IgAN (FIG. 2).

Like immunoglobulin IgA Fc, the rIgA analog adapts a duplex fold (FIG. 1B). Antibody IgA consists of two heavy chains and two light chains is conventionally referred to as monomeric IgA, whereas two IgAs further connected by a J-chain subunit are regarded as dimeric IgA. To avoid any confusion in terminology, the rIgA duplex is referred to as mono-rIgA in reference to immunoglobulin IgA. Biotin-rIgA was induced to form a stable poly-rIgA complex in association with tetrameric streptavidin, consisting of ~8 rIgA subunits (FIG. 1C, 1D, 1E).

It was expected that this poly-rIgA analog would resemble sterically clustered IgA-binding of pathogens, in which the Fc segments are configured to interact with CD89 of immune cells for phagocytic clearance. Through an avidity effect, the clustered pattern of Fc in synthetic poly-rIgA, even in the absence of pathogen, can trigger immune reactivity, including activation of alternative complement pathway, as seen by IgA immune complexes in human disease. Nevertheless, unlike natural IgA, this rIgA analog does not contain glycans to activate complement via MBL/lectin pathway.

Figure 3C:
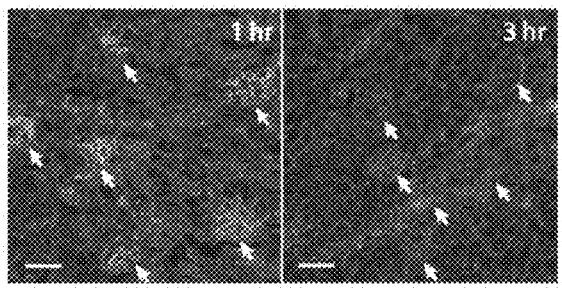
Figure 3D:
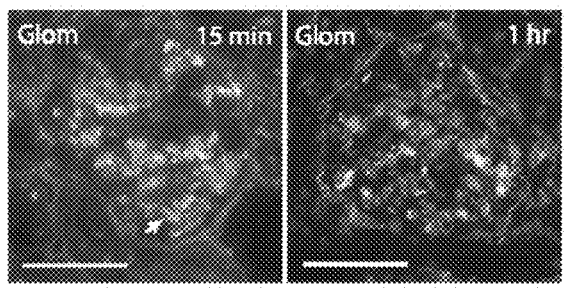
Figure 3E:
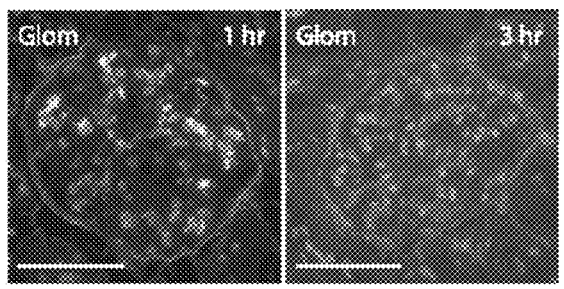
Figure 3F:
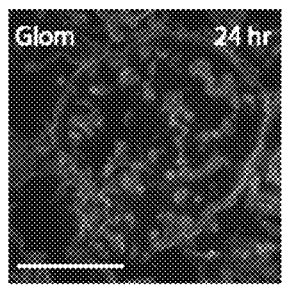
Figure 3G:
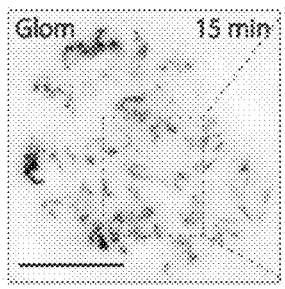
Figure 3G:
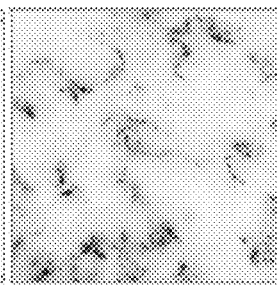
Figure 3G:
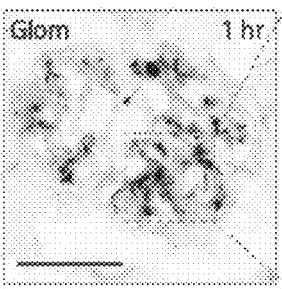
Figure 3G:
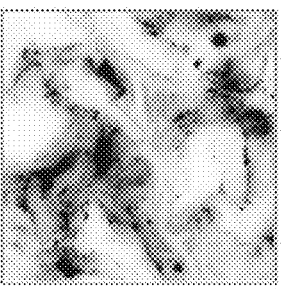
Figure 3H:
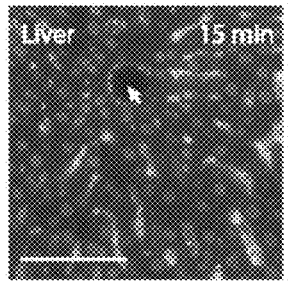
Figure 3H:
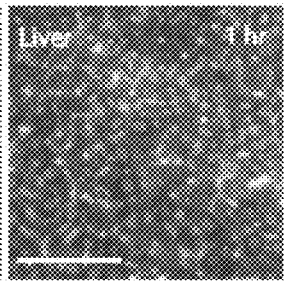
Figure 3H:
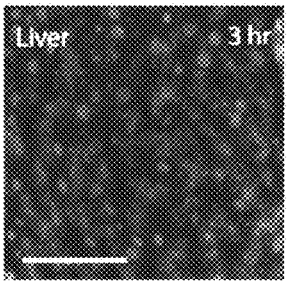
Figure 3H:
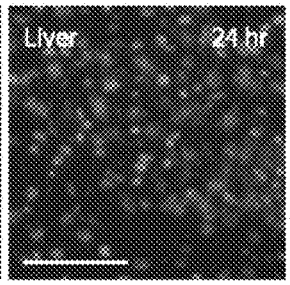

Example 2: Kinetics of Streptavidin-Induced Poly-rIgA Following a Bolus Injection in Rats Referring now to FIG. 3, systemic and targeted deposition and clearance of poly-IgA in rats after single dose injection is demonstrated. FIG. 3A demonstrates a schematic for bolus i.v. injection of poly-rIgA (open arrow), or mono-rIgA control (see also FIG. 4), was administered in rats. Time series samples of blood, kidney and liver were collected (arrowheads). Levels of rIgA in the specimens were detected using anti-IgA antibody (broken arrows). In FIG. 3B, following injection, serum samples were collected by tail bleeding and the poly-rIgA contents were measured by ELISA. Following a high initial concentration, the levels rapidly dropped to below 5% after twenty minutes. FIG. 3C and FIG. 3D. Comparison of poly-rIgA deposition between the two kidneys harvested at different timepoints from the same animal by unilateral nephrectomy. Close-up views of single glomeruli (Glom) were compared between fifteen minutes and 1 hour in FIG. 3C, and between 1 hour and 3 hours in FIG. 3D. Overall, there was a gradual reduction of poly-rIgA signals during this time. In FIG. 3E, one hour after poly-rIgA injection, exclusive signals were detected in all glomeruli (arrows), whereas other structures such as tubules and non-glomerular blood vessels remained negative. By 3 hours, the glomerular deposits were barely detectable. Scale bars: 50 µm. In FIG. 3F, by twenty-four hours, poly-rIgA deposits in the glomerulus were not detectable by immunofluorescence. Beside overall intensity that changed overtime, there were also noticeable changes in the pattern of poly-rIgA deposits (FIG. 3G). Single channel immunofluorescence staining of poly-rIgA substantiated the contrasting differences between fifteen minutes and one hour. At fifteen minutes, the deposits appeared in smaller puncta with some formed half circles, indicating capillary wall and paramesangium deposition. At one hour, the deposits had coalesced into large aggregates along the mesangium (compared inset images: follow dotted boxes). Poly-rIgA signals in the liver (FIG. 3H) also followed time-dependent changes in terms of intensity and pattern of distribution. At fifteen minutes, poly-rIgA staining was mostly along the direction pointing towards the central vein (arrow), consistent with the locations of the Kupffer cells along the sinusoid. By one hour and three hours, most hepatocytes were stained positive for poly-rIgA with a gradual decline of signal intensity over time. By twenty-four hours, little poly-rIgA was stained in the liver.

To further analyze the in vivo response to SA-induced poly-rIgA following i.v. injection in rats, the kinetics of poly-rIgA in systemic circulation were analyzed. Blood samples in a time series were collected and rIgA levels were measured by ELISA. Poly-rIgA followed fast clearance from circulation (FIG. 3B). By twenty minutes, serum rIgA dropped to below 5% of the levels at the beginning. After three hours, rIgA was no longer detectable in blood.

In order to track the kinetics of poly-rIgA deposits in the kidney, two kidneys from the same rats were separately collected by performing unilateral nephrectomy at two post-injection timepoints, fifteen minutes versus one hour, and one hour versus three hours (FIGS. 3C, 3D and 3E). Injection of uninduced (mono-)rIgA control has no detectable IgA signals in the kidney (FIG. 4A-B), comparable to the uninjected control (FIG. 4). In contrast, at fifteen minutes or one hour after poly-rIgA injection, poly-rIgA signals were detected exclusively in the glomerulus (FIG. 3C-3E).

Specifically, FIG. 4 demonstrates injection of mono-rIgA in rats did not form renal deposits. Similar to FIG. 3, fifteen minutes, one hour and three hours following the injection, kidney was harvested for performing immunofluorescence detection of rIgA. Little mono-rIgA signal was present in the kidney (FIGS. 4A and B). FIG. 4C shows an uninjected control and FIG. 4D demonstrates liver staining.

All glomeruli were stained with only a slight variation in the overall intensity. At higher magnification, the granular deposits were detected first in paramesangial and capillary walls at fifteen minutes, and then they formed clustered puncta in the mesangial area at one hour (FIG. 3C). There was a large reduction of poly-rIgA signals after three hours as compared to one hour (FIGS. 3D and 3E), and by twenty-four hours, no deposits were detected in the kidney (FIG. 3F). It is plausible that the bulk of renal deposits occurred within the first hour, and the reduction of signal intensity in the kidney by three hours was mainly attributable to local clearance activities. Beside the noticeable reduction of staining signals, the distribution pattern of the deposits also evolved over time (Examples in FIG. 3G). At fifteen minutes, poly-rIgA formed small puncta in the glomerulus, with some appeared to be associated with capillary loops and paramesangium (inset). By one hour, the fine puncta mostly coalesced into larger aggregates, suggesting a dynamic movement of poly-rIgA deposits from capillary wall and paramesangium to interstitial mesangium. During this short period, PAS staining of all renal slices showed no cell proliferation or other pathologic changes (FIG. 5).

FIG. 5 demonstrates normal renal histology following single dose of poly-rIgA injection. Normal Glomerulus and tubular interstitial lesion were found with rats after one dose Poly-rIgA injection. In FIG. 5, the scale bar is 50 µm.

Figure 4A:
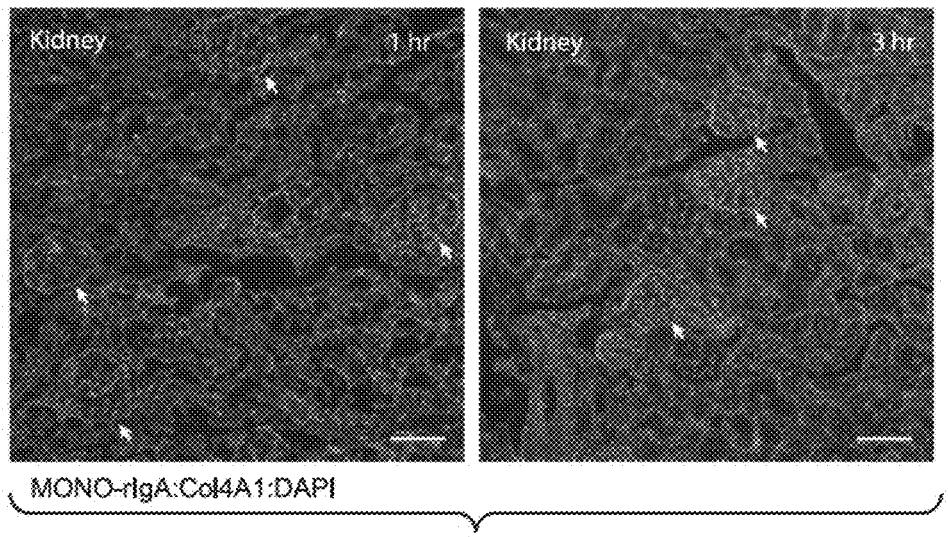
Figure 4B:
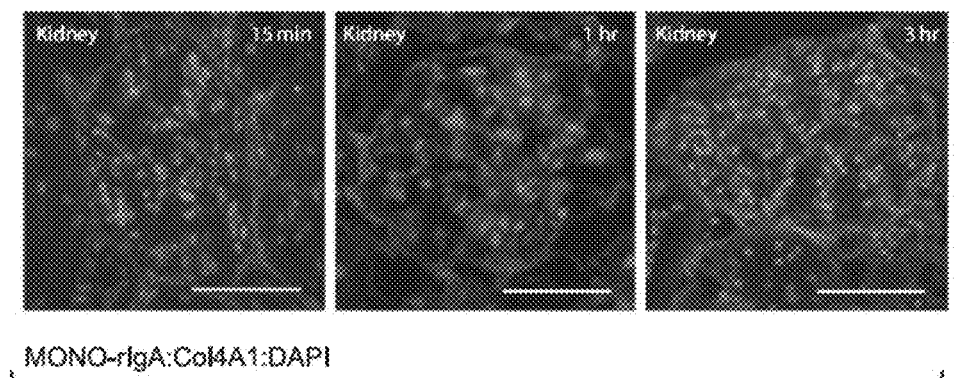
Figure 4C:
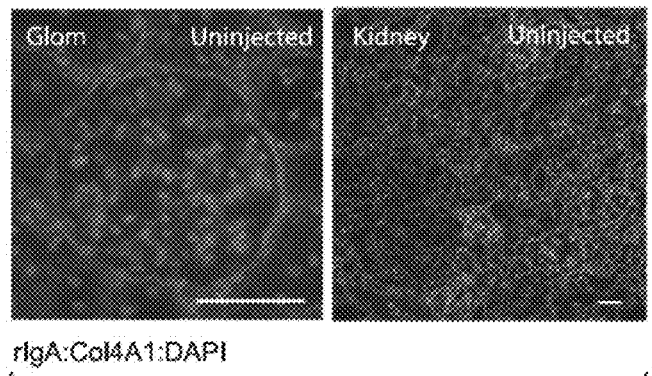
Figure 4D:
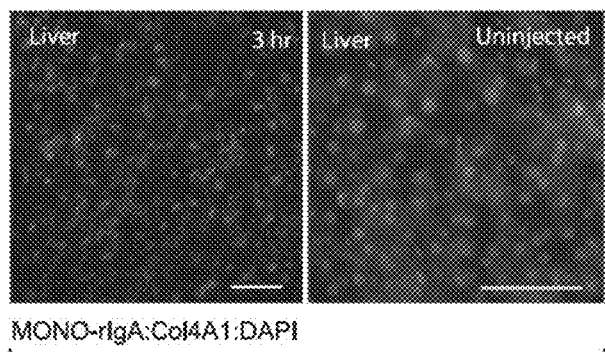

In the liver, poly-rIgA staining first appeared in the Kupffer cells fifteen minutes after injection along the sinusoids (FIG. 3I). After an hour, prominent staining signals could be seen in hepatocytes, suggesting Kupffer cells transported proteins to the hepatocytes across the fenestrated endothelial layer. By three hours, little IgA signals were observable as poly-rIgA had been catabolized in the liver. Like in the kidney, mono-rIgA had little presence in the liver (FIG. 4D).

Example 3: Renal Deposition and Clearance Following Repeated Injection of Poly-rIgA Referring now to FIG. 6, schematics of mesangial IgA deposits during the years-long disease course of IgAN (FIG. 6A) versus short poly-rIgA injection model are shown. The clinical course of IgAN follows chronic progression with flare-up episodes after infections. The dynamics of intrarenal clearance of deposits are unknown. In FIG. 6B, the synthetic model allows to study these dynamics with regard to the rate of deposition and clearance in a controlled fashion. Although our bolus poly-rIgA model has the unique advantage for examining the dynamics of clearance, the condition is different from the disease process of IgAN, in which pathogenic poly-IgA complexes are constantly present in blood (FIG. 6). Without wishing to be bound by theory, it has been theorized that IgA deposits in the glomerulus represents the equilibrium between new deposition and their clearance.

Figure 7B:
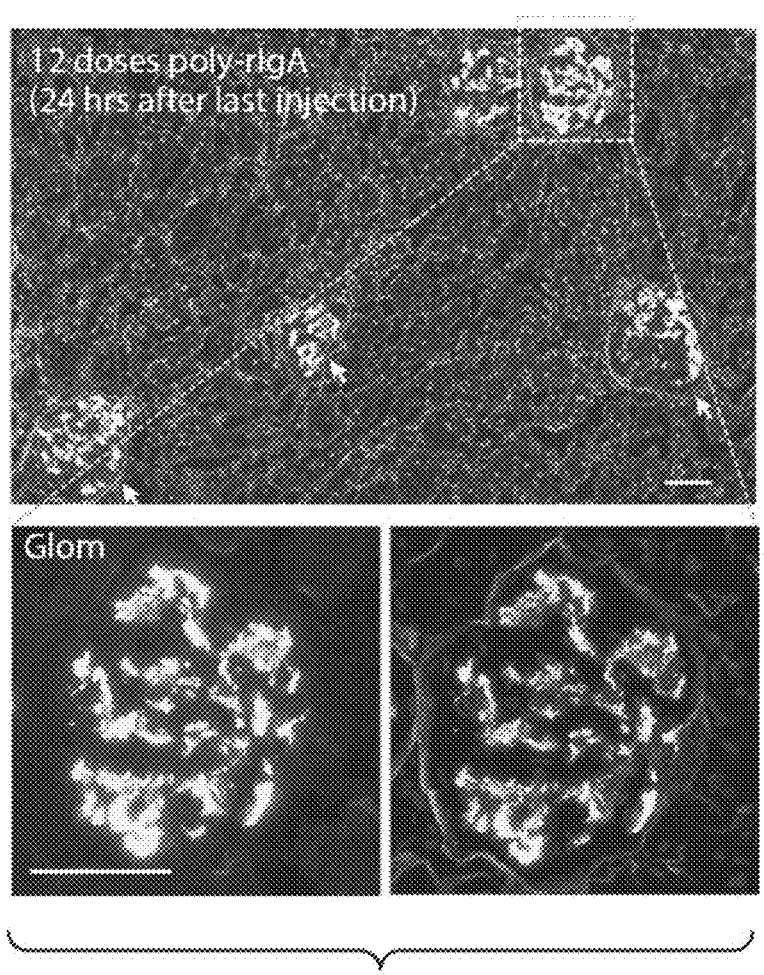
Figure 7C:
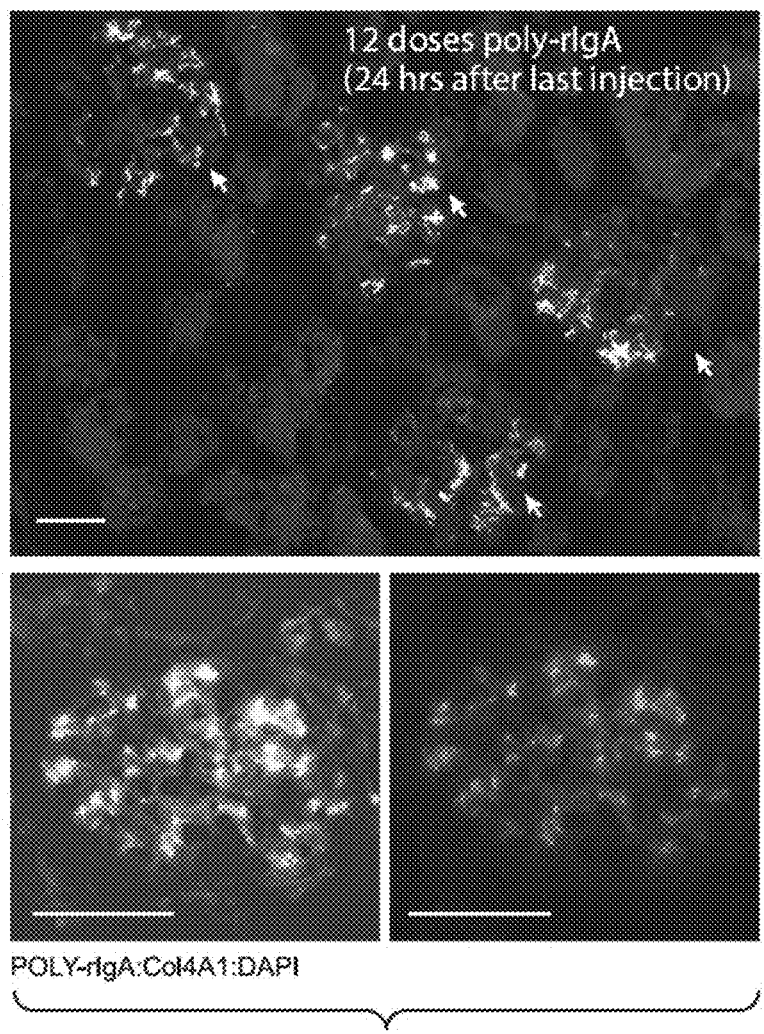
Figure 7D:
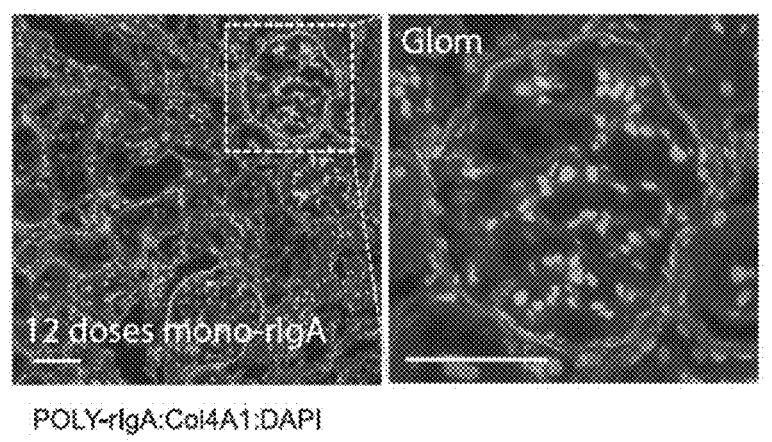
Figure 7E:
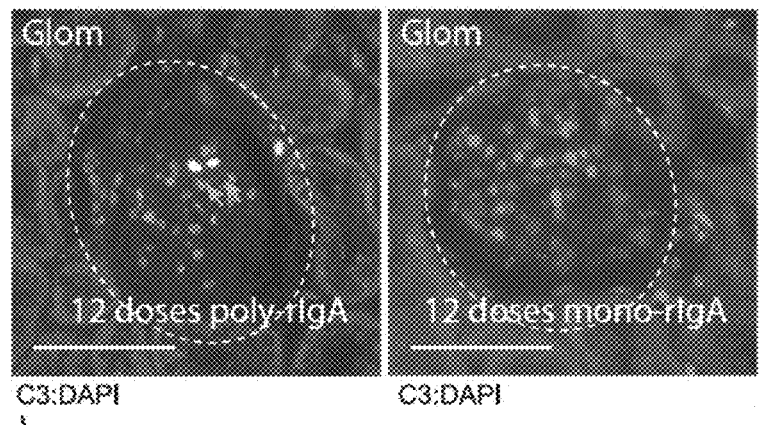
Figure 7F:
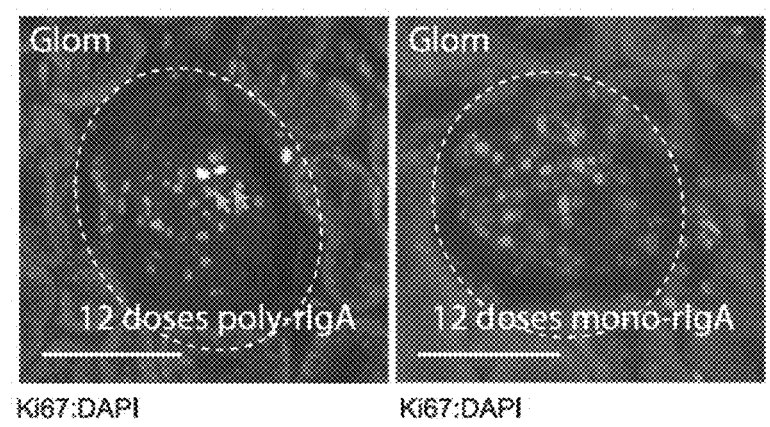

Having observed quick clearance of poly-rIgA by twenty minutes in circulation and mostly by three hours in the kidney (FIG. 3B and FIG. 3D), longer term studies were conducted. Referring to FIG. 7, consecutive daily injections of poly-IgA induced strong and long-lasting IgA deposits in glomerular mesangium is demonstrated. Specifically, in FIG. 7A, a cohort of rats was subjected to daily injection of either poly-rIgA (from streptavidin(SA)-induction), or mono-rIgA (uninduced), for twelve consecutive days. Twenty-four hours after the last injection, kidneys were collected for immunofluorescence (IF) staining of rIgA, IgG deposits in the kidney, complement C3 and cell proliferation marker Ki67. In FIG. 7B, rats that received poly-rIgA doses had intense staining of rIgA deposits exclusively in the glomerulus (arrows). Scale bar: 50 µm. Insets of a single glomerulus (Glom: lower panels) showed staining mainly concentrated in mesangial regions with some on capillary walls (with Col4A1 and DAPI counterstains). As shown in FIG. 7C, IgG co-deposition with IgA exclusively in the glomerular (arrows) mesangium and fewer capillary loops twenty-four hours after twelve consecutive daily poly-rIgA injections. FIG. 7D demonstrates, in contrast, little rIgA signals were in the kidney in rats that received injection of mono-rIgA (section overview in left panel and inset that detailed a single glomerulus in right panel). FIG. 7E indicates C3 deposits in the glomerulus (circled) were evident in rats injected with poly-rIgA. C3 signals were completely absent in glomeruli of mono-rIgA-injected rats (right panel), in contrast to positive signals in surrounding tubules. Antibody Ki67 was used to detect nuclei of proliferating cells. Two adjacent Ki67-positive nuclei were shown (white nuclei: pointed by arrows on DAPI counterstain) in the glomerulus of poly-rIgA-injected rats (FIG. 7F). Rats received control injection of mono-rIgA had no Ki67 positive glomerular cells, as expected.

Thus, having observed quick clearance of poly-rIgA by twenty minutes in circulation and mostly by three hours in the kidney (FIG. 3B and FIG. 3D), in other experiments injections were repeated doses every twenty-four hours for a total of twelve days (FIG. 7A). Animals were euthanized 24 hours after the last injection of poly-rIgA. In stark contrast to the single dose study that showed no IgA deposits 24 hours later (FIG. 3F), rats that received 12 doses of SA-induced poly-rIgA had accumulated strong deposit signals in all glomeruli (FIG. 7B).

Referring now to FIG. 8, immuno-fluorescence staining of poly-rIgA deposits in the kidney are demonstrated. After twelve consecutive doses of poly-rIgA injection. Insets showing mesangial and endo-capillary deposits (FIG. 8A). Renal poly-rIgA deposition following single bolus injections (FIG. 8B). Thus, in addition, the repetitive injections seemed to cause fusion of deposits into larger aggregates, with the major appearances in the mesangium, reminiscent of findings in patients with IgAN. There were also segmental granular capillary wall deposits (FIG. 7B and FIG. 8A).

This observation suggests a possible seeding effect of the IgA deposits that can prime the accumulation of new deposits in subsequent injection rounds. This is in contrast to the liver that had trace remaining IgA signal twenty-four hours after the last of the twelve doses as exemplified in FIG. 9 demonstrating trace rIgA in the liver after twenty-four hours following twelve consecutive doses of poly-rIgA injection (Scale bar: 50 µm). As negative control, daily injection of mono-rIgA for twelve days did not accumulate in the kidney (FIG. 7D and FIG. 8B), in keeping with the understanding of IgA-deposition mainly by polymerized IgA immune complexes.

Mesangial IgG co-deposition with IgA was found in all kidney tissues (FIG. 7C) and complement C3 positivity was evident in two of five rats that received twelve doses of poly-rIgA (FIG. 7E). In addition, Ki67 antibody were used to detect proliferating cells. All four rats injected with poly-rIgA had Ki67-positive nuclei in the glomeruli (FIG. 7F), indicating active cell proliferation. Neither uninjected controls nor mono-rIgA injected rats showed C3 or Ki67 positivity in the glomerulus (FIGS. 7E and 7F).

Example 4: Kidney Clearance of Chronic Poly-rIgA Deposition

Referring now to FIG. 10, kinetics of intraglomerular clearance of poly-rIgA deposits were analyzed. In FIG. 10A, a new cohort of rats was first treated with daily injection of poly-rIgA for twelve consecutive days. The rats were then left untreated for recovery during the remaining time of observation. Kidneys were collected on days three, six and fourteen after the last injection of poly-rIgA. FIG. 10B-D are representative examples of renal rIgA deposition. Deposits were stained strongly on day three and day six of recovery. By day fourteen, only very low levels of glomerular poly-rIgA deposition were detectable.

Having observed the effects of repeated doses of poly-rIgA on chronic deposition, a new cohort of rats to study the kinetics of intrarenal clearance were provided. As before, initially the same twelve-day injection schedule was followed. After the last injection of poly-rIgA, individual rats were harvested either three, six or fourteen days afterward, giving the time for the rats to recover without additional poly-rIgA loads (FIG. 10A). In striking contrast to the fast clearance following single injection that by three hours the majority of deposits disappeared (FIG. 3E), rats that had received twelve consecutive doses of poly-rIgA retained strong signals of glomerular mesangial IgA deposits for 6 days (FIGS. 10B and 10C). After the rat recovered for fourteen days without receiving new injections, low levels of IgA deposits remained detectable, albeit with greatly reduced intensity (FIG. 10D). Meanwhile, glomerular IgG deposits also subsided as demonstrated in FIG. 11. FIG. 11 demonstrates time-dependent clearance of IgG co-deposition in rat kidney. Following twelve consecutive daily dosages of poly-rIgA, the rats were allowed to recover for three, six or fourteen days. On day three and day six, poly-rIgA and IgG co-deposits were visible in the glomerulus (arrows). By day fourteen, both poly-rIgA and IgG staining had disappeared (Scale bar: 5 µm)

Example 5: Renal Histology Following Consecutive Poly-rIgA Doses

Referring now to FIG. 12, mesangial expansion and hypercellularity in poly-rIgA-injected rats is demonstrated. In FIG. 12A, Periodic Acid-Schiff (PAS) staining of rats kidney sections were performed to detect histologic changes to the glomerulus following no treatment, mono-rIgA injection for twelve days, poly-rIgA injection for twelve days, or poly-rIgA injection for twelve days and recovery for additional fourteen days. For each condition, two representative examples of glomerulus were shown (top and bottom). Overall, mono-rIgA-injected rats had the normal appearance of the glomerulus as compared to untreated controls. Meanwhile, poly-rIgA injection of rats caused histologic changes of the glomerulus that resemble some of the hallmarks in IgAN, namely hypercellularity of the mesangium (yellow arrows), matrix expansion (yellow star marking the widened purple matrices). In a particularly striking transformation, rats from poly-rIgA injection that were also allowed to recover for additional two weeks (fourteen days) showed a complete reversal of the glomerular lesions back to normal glomerulus appearance. FIG. 12B is a statistical analysis of hypercellularity of the mesangium among poly-rIgA, mono-rIgA and uninjected groups. Mean mesangial cell number (y-axis) was counted with the consideration of variations of glomerulus areas in the sections. The poly-rIgA group that received twelve doses of injection had the highest numbers of glomerular mesangial cells as compared to the control groups (triple asterisks: $p<0.001$).

Compared to the mono-rIgA and the uninjected groups, rats received twelve doses of poly-rIgA showed histologic changes reminiscent of IgAN pathology. These included overt mesangial hypercellularity and increased matrix in the glomerulus, in addition to significantly narrowed capillary loops (FIGS. 12A and 12B, and FIG. 13). FIG. 13 demonstrates renal histology features after twelve consecutive doses of poly-rIgA or mono-rIgA. Mesangial proliferation and matrix expansion were induced by poly-rIgA injections, two out of five rats had protein casts in the tubulointerstitium (FIG. 13A) and normal renal histology after twelve doses of mono-rIgA (FIG. 13B). Scale bar: 5 µm.

No observation of inflammatory cell infiltration, crescent formation, or segmental glomerulosclerosis of the glomerulus. While two rats had protein casts and the loss of tubular brush borders, other animals did not show evidence of interstitial or tubular damage (FIG. 13).

Interestingly, PAS staining of the recovery kidney showed normalized number of mesangial cells, reduced matrix staining signals, and normal glomerular capillary tufts (FIG. 12A). These results clearly demonstrated the intrinsic activities of the glomerulus not only removed chronic IgA deposits, but also self-healed to a great extent through remodeling mesangial scaffolds and the capillaries.

Referring now to FIG. 14, electron microscopy shows deposits in subendothelial and mesangial regions. In FIG. 14A, rats received twelve doses of poly-rIgA. Twenty-four hours following the last injection, the kidneys were collected for transmission electron microscopy (TEM). In FIG. 14B, TEM revealed structures including mesangial cells (MC), glomerular basement membrane (GBM: pointed by arrowheads), podocyte (pod) and podocyte foot processes (fp) (Scale bar: 5 µm). In FIG. 14C, at higher magnification, electron dense deposits (denoted by letter D) could be seen on the endothelial side of the basement membrane (left panel) and the mesangium (right panel).

Referring now to FIG. 15, electron microscopy of rat kidney after twelve injections of poly-rIgA. TEM overview of the glomerulus shows regions populated by mesangial cells (MC), density of irregular shape could be seen between mesangial cells. Basement membrane (BM: pointed by arrowheads), podocyte (pod) and foot processes (fp) appeared well preserved. Scale bar: 5 μm. At higher magnification, electron dense materials (denoted by letter D) could be seen on the endothelial side of the basement membrane (arrow). Foot processes (fp) appeared normal.

Transmission electron microscopy (TEM) analysis showed mesangial expansion by cells and matrix without abnormalities of podocytes and their foot processes (FIGS. 14A and 14B, and FIG. 15). The texture and thickness of the glomerular basement membrane (GBM) were also normal. Consistent with findings of immunofluorescence microscopy, there were large mesangial, subendothelial, or intraluminal densities and electron dense deposits (FIG. 7, FIG. 14C and FIG. 14D).

Example 6: Urinary Abnormalities of Casts, RBC, and Albuminuria

Referring now to FIG. 16, proteinuria, urinary sediments and serum creatinine analysis is provided. In FIG. 16A, PAS staining showed normal appearance of the tubule in uninjected and mono-rIgA-injected rats. The brush border on the luminal side was well preserved (purple). Two rats that received twelve doses of poly-rIgA developed tubular protein casts (asterisk). Rats were allowed to recover for fourteen days showed no albuminuria and no tubular casts. FIG. 16B demonstrates microscopic examination of the urinary sediments of the two albuminuric rats showed tissue clumps (arrowheads) that resembled urinary cases in patients. In addition, red blood cells (RBC) were visible (arrows), either in isolation or in association with the cast structures. FIG. 16C demonstrates urinalysis by SDS PAGE showed proteins in urine, including albumin (ALB), and normal low molecular weight urinary proteins such as MUPS and RUP. Urinary samples A and B were collected on different days from rat that received twelve doses of poly-rIgA. The quantity of urinary albumin was calculated based on bovine serum albumin standards (BSA). FIG. 16D indicates there was no significant difference of serum creatinine levels between rats following twelve doses of poly-rIgA injection and mono-rIgA injection. NS, Not Statistically Significant.

Despite of the glomerular deposition and matrix responses following twelve doses of poly-rIgA, two out of a total of five rats in the group had protein casts in PAS staining (FIG. 16A and FIG. 13). Urine samples collected on two different days showed continuous presence of RBC, urinary casts (FIG. 16B) and albuminuria calculated at ~0.5 g/L (FIG. 16C), which were consistent with urinalysis features of IgAN. No difference of serum creatinine levels was found in rats with either poly-rIgA or mono-rIgA injection (FIG. 16D), and glomerular filtration rate (GFR) of the rats having albuminuria was in normal range as measured by transcutaneous reading of sinistrin clearance.

Example 7: Poly-rIgA Binds and Activates Renal Mesangial Cells in Culture

It was previously demonstrated that poly-IgA extracted from clinical samples can stimulate cytokine production by human mesangial cells in culture. To examine the activity of synthetic poly-rIgA analog to human cells, a new rIgA derived from human IgA1 sequence with an N-terminal AviTag for biotinylation was constructed and recombinantly produced (referred to as h-rIgA1 or h-rIgA). Similar to its rat counterpart, biotinylated h-rIgA1 could be induced for oligomerization in the presence of streptavidin (SA)(FIG. 17).

FIG. 17 demonstrates human-derived poly-h-rIgA caused glomerulus deposition in mice. Recombinant 1gA Fc based on human 1gA1 heavy chain sequence fused to an AviTag was produced in HEK293 cells. This h-rIgA was expected to contain glycan attachments. Following biotinylation, h-rIgA was induced for polymerization by streptavidin (SA) as described before. SA-induction caused an up-shift in molecular weight (MW) as determined by size-exclusion chromatography (SEC) (dotted line to solid line). Injection of this poly-h-rIgA in mouse for five consecutive days resulted in renal deposition detected by anti-IgA staining (left panel). The staining was concentrated in glomerulus areas (arrows). In addition, staining of the kidney sections with Ki67 showed positive nuclei (arrows) within the glomerulus (circle), indicating active cell proliferation.

Referring now to FIG. 18, poly-IgA binds renal mesangial cells in culture is demonstrated. Human glomerular mesangial cells were cultured in dishes. Human biotin-h-rIgA either in the SA-induced polymeric (FIG. 18A) or uninduced monomeric (FIG. 18B) state was added to culture medium. Following washing to remove unbound h-rIgA, the cells were fixed and then probed for IgA contents. Phalloidin staining for Actin and DAPI for nucleus were the counterstains. While strong poly-h-rIgA signals were associated with the cells (in FIG. 18A), there was no specific binding of mono-h-rIgA detected (in FIG. 18B). In FIG. 18C, following co-culture of the cells with either poly- or mono-h-rIgA for overnight, the culture medium was harvested for detection of IL-6 by ELISA (y-axis). The inflammatory response of the cells in IL6 production to human poly-h-rIgA was significantly greater than that to mono-h-rIgA.

A binding assay was performed by adding SA-induced poly-h-rIgA1 or uninduced mono-h-rIgA1 to cultured mesangial cells (details in Methods). The results showed that poly-h-rIgA1, but not mono-h-rIgA1, bound the cells (FIG. 18A compared to 18B). Furthermore, poly-h-rIgA1 treatment of the cells stimulated more IL-6 production as compared to mono-h-rIgA treatment (FIG. 18C). Like rat-derived poly-rIgA, this h-rIgA1 of human also deposited in the glomerulus and induced mesangial cell proliferation following the injections in mice (FIG. 17B).

Example 8: Poly-IgA Activates Complement C3

Next, it was determined whether the synthetically oligomerized rIgA could activate complement to further potentiate inflammatory reactivity. Referring now to FIG. 19, it was demonstrated that poly-rIgA activates complement in vitro. In FIG. 19A, a rat poly-rIgA and mono-rIgA were separately incubated with freshly harvested rat serum. These 6×His-tagged rIgA proteins were then immobilized by Ni2+-NTA beads. Following elution with sample buffer. All proteins were resolved by SDS PAGE, which was subsequently examined by Western blotting (WB) with either anti-C3 or anti-IgA antibody (left and right panels, respectively). Several C3 bands were visible corresponding to C3bα, C3bβ and C3cα2. While there was no difference in C3bα and C3bβ amounts between poly- and mono-rIgA samples, C3cα2, the active C3 fragment, was prominently present with poly-rIgA. This was despite of lower levels of polyrIgA than mono-rIgA loading (right panel). Note there was a cross-reactive staining of r-IgA background/bkgr in the anti-rat C3 blot). The whole serum lane was a control. C3cα2 to rIgA ratios were calculated, showing C3cα2 association with poly-rIgA (FIG. 19B). A schematic model (FIG. 19C) for the pathogenesis of poly-IgA immune complexes in IgAN as revealed by synthetic poly-rIgA analog is presented. Top: Modified four-hits hypothesis showing Gd-IgA at the beginning, followed by immune complex formation either via anti-glycan antibodies or intrinsic instability of Gd-IgA prone to self-aggregation, or both. Dotted arrows indicate unclear mechanism(s). In the synthetic IgA/Fc analog model (bottom panel), recombinant Fc of IgA was induced to multimerize via biotin-streptavidin (SA) reaction. In this injection model of mono-versus poly-rIgA, the critical role of Fc multimerization was clearly demonstrated from a number of observations (in parentheses). This acute injection model, with the distinctions between single versus multi-dose injection, also raised questions regarding the intraglomerular processing of IgA deposits, as to whether memory priming, or factors that influence the kinetics of mesangial clearance.

Unlike natural poly-IgA that also contains non-IgA components such as IgG and other associated proteins, synthetically induced poly-rIgA is a much simpler analog. Complement C3 deposits in the glomerulus are present in majority of IgAN patients, attributable to an activating surface of the IgA complexes for binding C3 convertase (C3bBb). To elucidate the requirement of IgA's multimeric state in interactions between IgA and C3, complement activation experiments were performed by incubating either uninduced rIgA or SA-induced poly-rIgA with rat serum. Following Ni-NTA purification of mono-rIgA or poly-rIgA, C3 contents were detected by Western blotting. Immunoblotting showed multiple C3 fragments in association with mono-rIgA and poly-rIgA. However, the intensity of C3cα2 band was much stronger with poly-rIgA as compared to mono-rIgA (FIGS. 19A and 19B), indicating this poly-rIgA analog could directly activate C3 in serum. These results were consistent with the in vivo observation of C3 deposition following poly-rIgA, as opposed to mono-rIgA, injections (FIG. 7E).

Materials and Methods

Recombinant IgA Construction, Biotinylation and Streptavidin-Induced Polymerization In one aspect, an exemplary IgA Fc amino acid sequence fused with an AviTag may be that of SEQ ID NO: 1:

```
MDGLNDIFEAQKIEWHESCSLVCRPRLSLQRPALEDLLLGSEASLTCTLR

GLKEPTGAVFTWQPTTGKDAVQKEAVQDSCGCYTVSSVLPGCAERWNNGE

TFTCTATHPEFETPLTGEIAKVTENTFPPQVHLLPPPSEELALNELVSLT

CLVRGFNPKDVLVRWLQGNEELPSESYLVFEPLREPGEGAITYLVTSVLR

VSAETWKQGAQYSCMVGHEALPMSFTQKTIDRLSGKPTNVNVSVIMSEGD

GICY.
```

In one aspect a DNA sequence encoding a rat IgA $C_H2$-$C_H3$ segment or subsequence may be fused to an N-terminus AviTag sequence encoding amino acids GLN-DIFEAQKIEWHE (SEQ ID NO: 2). Clearly though, any IgA Fc region sequence can be use of for the injectable recombinant IgA of the invention. The fusion was cloned into PET30a vector (Invitrogen, Carlsbad, CA) with the addition of a 6×His purification tag. Recombinant protein production was in 200 mL culture of BL21 (DE3) strain of E. coli transformed with the vector.

Protein expression was induced with 0.3 mM isopropyl-β-d-thiogalactoside when the bacterial culture reached OD600 of 0.6-0.8. The culture continued for overnight at 16° C. Culture medium was removed by centrifugation and the bacteria pellet was store at −80° C. On the day of purification, the bacterial pellet was resuspended in 0.5M NaCl 20 mM $Na_2HPO4$ buffer (PH=7.4). After adding 0.5 mg/ml lysozyme for 30 min, followed by sonication, the mixture was subjected to 25,000 rpm centrifugation. The clear supernatant that contained AviTag-rIgA ran through a Histrap column (GE, Healthcare), and the recombinant protein was collected with elusion buffer containing 250 mM imidazole. The protein concentration was calculated using BCA kit (Pierce) and by running SDS-PAGE.

Purified rIgA has a natural tendency to form small amounts (up to 10-20%) of oligomers following week-long storage due to disulfide interactions. In order to reduce the interference by these oligomers, three hours before each injection of rats mono-rIgA was repurified by running size-exclusion chromatography (SEC: Superdex S-200, GE, Healthcare).

Due to its poor solubility in bacterial expression, human recombinant IgA1 (h-rIgA) was alternatively produced using mammalian cell stable expression system. Human IgA1 $C_H2$-$C_H3$ cDNA fused to sequences encoding IL-2 signal peptide, 6×His and AviTag in this order at the 5'-end was cloned into pcDNA3 vector (Invitrogen, Carlsbad, CA). Human embryonic kidney (HEK293) cells (ATCC) were transfected with the plasmid using Lipofectamine 2000 (Invitrogen). Twenty-four hours after transfection, the cells were serial diluted into 100 mm dishes and maintained in selection medium containing 1 mg/mL G418 (Thermo Fisher Scientific, Waltham, MA). Selection medium was replaced every 3 days for 14 days when cell clones were visible. These clonal cell masses were individually seeded into new 24-well plates for further amplification. The clonal cell lines that expressed the highest levels of His-AviTag-h-rIgA(Fc) in culture medium were identified by immunoblotting against human IgA Fc using a horseradish peroxidase (HRP)-conjugated goat anti-human IgA polyclonal antibody (Bio-Rad).

BirA biotin ligase was produced using BL21 (DE3) expression system. Purified rIgA protein that contained either human or rat IgA Fc sequence fused to an AviTag was subjected to site-directed biotinylation. The reaction occurred in 0.2 mM ATP, 5 μM $MgCl_2$ supplemented with BirA as described by Fairhead and Howarth. The reaction was stopped by column desalting (Thermo Fisher Scientific). In theory, each polypeptide was labeled with one biotin moiety. To induce oligomerize this biotin-conjugated rIgA, streptavidin was then added at a 1 to 4 molar ratio. The molecular size of induced polymer rIgA was tested with SDS PAGE and gel filtration by Superdex S-200 Increase 10/300 column (GE Healthcare). Because small quantity of spontaneously aggregated rIgA exist after week-long storage, monomer rIgA was repurified from stock with Superdex S-200 column 3 hours before each injection.

Rat Experiments

Mono-rIgA or streptavidin-induced poly-rIgA were injected to 10-weeks old male Wistar rats (Charles River Labs). Injection of the rat tail vein used a 24 Ga stylet-guided catheter (Exel Int.). Single bolus injections were with the dose at 2 mg/kg. Time series blood samples were collected by tail bleeding before and after rIgA injection. For determine the kinetics of renal deposition and clearance, a unilateral nephrectomy was performed at 1 hour and 3 hours after injection from same rats. Long-term injection dose was at 4 mg/kg, with 4 rats in each group to received daily injections of either mono-rIgA or SA-induced poly-rIgA for 14 consecutive days. To estimate the duration required to clear the renal deposits after receiving 14 doses of poly-rIgA, were harvested the kidneys of rats in the group 2 to 14 days after the last dose of SA-rIgA.

SDS PAGE, Western Blotting, and ELISA

Purified rIgA samples were either boiled in SDS-PAGE sample buffer (Bio-Rad Laboratories, Hercules, CA) supplemented with or without TCEP (reducing or nonreducing condition respectively). The samples were resolved by 4-12% SDS-PAGE gel (Bio-Rad Laboratories) and either stained by GelCode Blue (Thermo Fisher Scientific) or transferred to PVDF membrane for Western blotting. The membrane was blocked with 5% non-fat milk for 1 hour at room temperature, and then blotted with HRP-conjugated goat anti-rat antibody (Abcam) goat anti-human IgA HRP antibody (SouthernBiotech) for detecting IgA Fc. The membrane was washed with PBST and developed using the Clarity™ ECL substrate (Bio-Rad Laboratories). Rat urine samples before and after intervention were also collected for albuminuria test by SDS-PAGE.

For detecting the binding between rIgA and CD89, 6×His tag fused rat CD89 recombinant protein (Sino Biological) was incubate with rat serum and human IgA1 (RayBiotech) at 4° C. for overnight. 6×His-selective nickel magnetic agarose beads (Sigma-Aldrich) were used to capture 6×His tagged CD89. Western blot was conducted to detect IgA using HRP-conjugated goat anti-rat antibody (Abcam) goat anti-human IgA HRP antibody (SouthernBiotech) respectively.

Quantitative detection of rIgA was by ELISA. As capturing antibody, 2.5 µg/ml mouse anti-6×His tag antibody (Thermo Fisher) was used to coat ELISA plate at 4° C. overnight. The plate was blocked with 1% BSA/TBST and incubated with purified 6×His-tagged rIgA as standards or diluted serum 1:25 in 0.1% BSA/TBST buffer for 2 hours at room temperature. Then rIgA was detected using goat anti-rat IgA-HRP antibody (Abcam) followed by TMB substrate. Absorbance was measured at 450 nm and concentration of rIgA protein was calculated with Logistic four parameter regression curve.

Histopathology, Glomerulus Filtration Rate and Urinary Sediments Examinations

Kidneys and livers were quick-frozen in OCT (Thermo Fisher Scientific) or fixed in 10% neutral-buffered formalin (Sigma-Aldrich) for immunofluorescence and PAS staining, respectively. Frozen kidneys were sectioned at 4 µm for IgA, C3, and Ki67 detection using goat anti-rat IgA antibody (Bio-Rad Laboratories) at 1:100 dilution, rabbit anti-C3 antibody (Proteintech) at 1:100 dilution, and rabbit anti-Ki67 antibody (Thermo Fisher) at 1:250 dilution, respectively. Anti-collage IV a1 (1:500 dilution from Novus) were used as counterstaining. Frozen livers were sectioned at 4 µm for goat anti-rat IgA (Biorad 1:100 dilution) and rabbit anti-CD31 (Sigma 1:100 dilution) staining. The fixed tissues were embedded in paraffin and sectioned at 2.5 µm using Leica Microtome. The sections were stained by Periodic Acid Schiff (PAS) (Thermo Fisher) according to the manufacturer's instruction. The PAS stained sections were scanned by Olympus microscope. The average number of mesangial cells per glomerulus area was derived from 20 glomeruli per kidney in PAS section. Immunofluorescence staining were scanned using Ti2 Widefield microscope. For electron microscopy of kidney sections, renal cortex was fixed in 2% glutaraldehyde and 4% paraformaldehyde in 0.1M PBS buffer. Dense electron deposition and renal morphology were evaluated by transmission electron microscopy (TEM).

Glomerulus filtration rate (GFR) of animal with proteinuria was detected using transcutaneous reading of sinistrin clearance (2)(Mannheim Pharma & Diagnostics). For urinalysis, after collection fresh urine was centrifuged at 1000 rpm, and urinary sediments were examined with inverted phase contrast microscope (Nikon).

Mesangial Cell Stimulation and Binding of Human Poly-rIgA1

Primary human mesangial cells were a gift from Dr. Tomoko Hayashida at Northwestern University, and were incubated in mesangial cell medium with 5% fetal bovine serum and 1% mesangial cell growth supplement (Scien-Cell). When cells grown to 80% confluency (passage 7), the cells were starved for overnight in 0.05% fetal bovine serum 0% mesangial cell growth supplement in mesangial cell culture medium. On the next day, cells were stimulated with mono-rIgA1, SA-induced poly-rIgA1 (200 µg/ml), or control for 48 hours in 12-well tissue culture dishes. Supernatant was collected for measuring IL-6 levels by ELISA (R&D Systems). To determine the binding of human rIgA1 to mesangial cells, the same cells were washed with cold PBS for three times and then preincubated on ice for 15 minutes with 1% BSA/PBS. Then 100 ug of either mono-rIgA1 or SA-induced poly-rIgA1 was added to the medium for one hour on ice. Then the cells were washed three times with PBS and fixed with 4% PFA for 10 minutes at room temperature. After blocking specimens with 3% BSA for 30 minutes at room temperature, binding of h-rIgA1 was detected by using goat anti-human IgA antibody (SouthernBiotech) at 1:100 dilution, followed by secondary donkey anti-goat IgG 550 (Sigma-Aldrich). Phalloidin (Life Technologies) staining of F actin and DAPI (Sigma-Aldrich) staining of nuclei were used as counterstains.

In Vitro Complement Activation Assay

To examine complement activation by SA-induced poly-rIgA, 20 µg of either mono-rIgA or poly-rIgA was incubated with or without 20 µl of freshly collected rat serum at 37° C. for 2 hours. The mixture was then diluted with PSB to 500 µl. Nickel magnetic agarose beads (Sigma) were used to capture the immunoprecipitation (of 6×His-tagged rIgA). Activated complement C3c α2 fragments were visualized by Western blotting using rabbit anti-rat C3 antibody (Proteintech). The loading amounts of mono-rIgA and SA-induced poly-rIgA were determined via goat anti-rat IgA HRP antibody (Abcam) as controls.

Conclusion

Although the molecular pathogenesis for IgA nephropathy may be unclear, increasing evidence suggests a causal role of IgA1 immune complexes in circulation. Following a synthetic approach, a higher-order (8× and above) oligomeric rIgA heavy chain that resembles native poly-IgA was produced. Mono-rIgA was constructed with an N-terminal biotin-tag, which reacts to streptavidin (SA) to form stable poly-rIgA. Using these simple rIgA analogs to inject rats, there was striking differences between mono- and poly-rIgA. Only the latter formed deposits in the glomerulus, subsequently causing histologic lesions such as mesangial hypercellularity and matrix expansion. The result suggests homo-oligomeric rIgA alone is sufficient to cause renal deposition. The kinetics of poly-rIgA deposits as being cleared from mesangium and observed an apparent priming effect of prior deposits to facilitate the formation of new deposits. Using this injection model, also observed was a time-dependent intraglomerular clearance of its poly-rIgA deposits, taking as long as two weeks to remove chronic deposits. In this process, histologic remodeling within the glomerulus also occurred with reduced matrix materials and normal capillary tufts (model in FIG. 19C). These results demonstrated histological plasticity of the glomerulus following the clearance of deposits, thus realizing the possibility of renal improvement in IgA nephropathy with effective therapeutic intervention.

IgA nephropathy is considered a chronic disease and individuals may follow different clinical courses of progression. New evidence from renal graft biopsy showed prevalence of latent IgA deposits. These donors and their kidneys were otherwise considered healthy, suggesting a possibility that dynamic IgA deposition and clearance constantly occur. As it is rare to frequently biopsy IgAN patients, the extent of balance between deposition and clearance is not known (FIG. 6A). Nonetheless, indirect evidence suggests the glomerulus may have the intrinsic potential in either coping with or clearing deposits. IgAN patients often experience disease flare-ups as indicated by short hematuria and proteinuria episodes during times of infection. By contrast, in pediatric IgA vasculitis/HSP with renal involvement, recurrent chronic IgAN is rare. Not wishing to be bound by theory, a constant exposure of kidney to circulating IgA immune complexes may be a key in IgAN pathogenesis. In cases of rapidly progressive renal failure due to IgAN, plasmapheresis occasionally renders relieve of the clinical symptoms, suggesting the contribution of new deposits to disease progression. Conversely, in renal transplantation due to IgAN, there is high recurrence rate despite of immuno-suppressing therapy for controlling graft rejection. Our model using synthetically generated recombinant poly-IgA analog (poly-rIgA) allowed us to investigate conditions that contribute to net gain in deposition, as counterbalanced by observed systemic and intrarenal clearance of IgA complexes (FIG. 6B). Specifically, the priming—or seeding— effect of existing deposits in accelerating the formation of new deposits might be relevant to the basis of IgAN flare-ups in patients.

Most earlier mouse models of IgAN, either spontaneous or genetic, have constant levels of plasma IgA. It is often difficult to examine the dynamic balance, if exists, between mesangial deposition of IgA and its local clearance. In addition, those IgAN models are mostly based on massively elevated plasma levels of IgA, sustained at up to 50~100 times of normal levels. It is plausible that only the harmful IgA complexes, which levels are expected to be proportionally higher than normal in these models, are the source of deposits. While it is also speculated that particular proteins in IgA complexes may dictate its renal affinity, these high-IgA models may not be able to address this probability. Our synthetic analog model, in which polymeric complexes can be induced using streptavidin, clearly demonstrated that poly-IgA alone is sufficient to form renal deposits that resemble those found in IgAN biopsy. In contrast to the spontaneous or genetic models, our synthetic model with the injection of streptavidin-induced poly-rIgA had only a small percentage increase in the combined IgA levels—The poly-rIgA amount is calculated as ~2.5% of endogenous IgA.

With respect to the polymer size of rIgA needed for renal deposition, our SA-induced complexes have the ability to present variable numbers of rIgA subunits. Although our single-chain rIgA naturally forms duplex—just like its natural IgA counterpart—and streptavidin binds four biotins, dimeric rIgA chains may still have their two individual biotin tags either bind the same streptavidin, or separately bind two streptavidin molecules. In the latter configuration, one complex contains two streptavidins with up to 4×2−1=7 dimeric IgA attached to them as exemplified in FIG. 20.

Specifically, a variety of multimeric states of poly-rIgA induced by streptavidin. FIG. 20A. Like its antibody counterpart of IgA heavy chain, recombinant IgA Fc/CH2-CH3 naturally forms a dimer. Through the N-terminal biotin tag (solid triangle) of one of the Fc chains, the duplex molecules interact with streptavidin (SA), which is a tetramer. Therefore, a 4× poly-rIgA is formed. Similarly, each biotin tag of the rIgA duplex can separately interact with two SAs, which further bind additional biotin-rIgA to form 7× poly-rIgA (FIG. 20B). In the case of mixed binding modes between SA and the biotin tags, 3× poly rIgA can form (FIG. 20C). Size-exclusion chromatography (SEC) showed at least three major spikes, which possible represented 2×, 4× and 7× of rIgAs as the dominant contents. It should also be noted that not only natural IgA can be detected in their complex forms, which are expected to be pathogenic, our uninduced IgA analog also spontaneously aggregate into higher-order oligomers, forming a small high-molecular-weight peak in SEC (FIG. 21). FIG. 21 indicates recombinant mono-rIgA contained a small fraction of polymers from self-aggregation. By running size-exclusion chromatography (SEC), a small fraction of self-aggregated poly-rIgA of ~400 kDa was detected (between dotted lines). For rat injection experiments, only the 64 kDa mono-rIgA was used. In animal injection experiments, an initial step of repurifiying mono-rIgA immediately before injecting in rats, and there was no renal deposition from mono-rIgA, in stark contrast to SA-induced poly-rIgA that readily formed renal deposits.

In some aspect, there were distinctions between mono- and poly-rIgA analogs in in their affinities to the glomerular mesangium and to C3cα2, an active C3 fragment, without wishing to be bound by theory, it may be a simple avidity effect that drives these interactions, with the clustered presence of IgA collectively gathering the strength of multivalent interactions to mesangial matrices and complements. Similar reasoning can be applied to the perceived poly-rIgA and IgG interactions in the kidney.

The strength of the synthetic model is that it depicts the early events of mesangial deposition by polymeric IgA. Through timed injection of the synthetic analog, the model allowed us to delineate the intricate balance between deposition and clearance, in which a strong priming activity of mesangial deposits in inducing new deposition, or impeding clearance, or both, were observed.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A method of inducing IgA nephropathy in a subject comprising:

providing a polymeric complex of unglycosylated IgA CH2-CH3 oligomeric fragments, wherein each of the IgA CH2-CH3 oligomeric fragments comprises a biotin moiety at the N-terminus of the IgA CH2-CH3 and the polymeric complex is formed by the addition of streptavidin to a mixture of biotinylated IgA CH2-CH3 oligomeric fragments; and daily, intravenous administering to a subject the polymeric complex of unglycosylated IgA CH2-CH3 oligomeric fragments, wherein the daily administration of the polymeric complex to the subject for a period of twelve consecutive days induces in the subject kidney glomerulus mesangial deposition of the polymeric complex of unglycosylated IgA fragments and induction of renal and systemic responses toward clearance of the polymeric complex from the kidney, the deposition of IgA polymers and renal and systemic responses toward clearance of IgA polymers being indicators of a IgA nephropathy, wherein the subject is a rodent.

2. The method of claim 1 wherein the polymeric complex is homo-oligomeric.

3. The method of claim 1 wherein the polymeric complex is about 200 kDa to about 800 kDa in size.

4. The method of claim 1, wherein the polymeric complex comprises two, three, four or seven IgA CH2-CH3 oligomeric fragments.

5. The method of claim 1, wherein the subject having induced IgA nephropathy demonstrates histologic changes of the glomerulus comprising mesangial hypercellularity, matrix expansion, narrowing of capillary loops, or a combination thereof.

6. The method of claim 5 further comprising determining the efficacy of a therapeutic agent for IgA nephropathy in a subject comprising:

treating the subject having induced IgA nephropathy with a therapeutic agent; and evaluating glomerulus mesangial deposition of the polymeric complex of unglycosylated IgA oligomeric fragments or histologic changes after treatment with the therapeutic agent thereby determining the efficacy of the therapeutic agent.

7. The method of claim 5 further comprising, determining the efficacy of a diagnostic method of IgA nephropathy in a subject comprising:

applying a diagnostic method to the subject having induced IgA nephropathy; and evaluating IgA indicators including glomerulus mesangial deposition of the polymeric complex of unglycosylated IgA oligomeric fragments or histologic changes in the subject to obtain a correlation between the diagnostic method and IgA indicators, thereby determining the efficacy of the diagnostic method.

8. A method for producing an IgA nephropathy animal model comprising:

providing a polymeric complex of unglycosylated IgA CH2-CH3 oligomeric fragments, wherein each of the IgA CH2-CH3 oligomeric fragments comprises a biotin moiety at the N-terminus of the IgA CH2-CH3 and the polymeric complex is formed by the addition of streptavidin to a mixture of biotinylated IgA CH2-CH3 oligomeric fragments and daily, intravenous administering to a subject the polymeric complex of unglycosylated IgA CH2-CH3 oligomeric fragments, wherein the daily administration of the polymeric complex to the subject for a period of twelve consecutive days induces in the animal kidney glomerulus mesangial deposition of the polymeric complex of unglycosylated IgA fragments thus inducing renal and systemic responses toward clearance of the polymeric complex from the kidney, thereby producing an animal model of IgA nephropathy, wherein the animal model is a rodent.

* * * * *

SEQUENCE LISTING

<160> NUMBER OF SEQ ID NOS: 2

<210> SEQ ID NO 1
<211> LENGTH: 254
<212> TYPE: PRT
<213> ORGANISM: Artificial Sequence
<220> FEATURE:
<223> OTHER INFORMATION: Synthetic

<400> SEQUENCE: 1

Met Asp Gly Leu Asn Asp Ile Phe Glu Ala Gln Lys Ile Glu Trp His
1               5                   10                  15

Glu Ser Cys Ser Leu Val Cys Arg Pro Arg Leu Ser Leu Gln Arg Pro
            20                  25                  30

Ala Leu Glu Asp Leu Leu Leu Gly Ser Glu Ala Ser Leu Thr Cys Thr
        35                  40                  45

Leu Arg Gly Leu Lys Glu Pro Thr Gly Ala Val Phe Thr Trp Gln Pro
    50                  55                  60

Thr Thr Gly Lys Asp Ala Val Gln Lys Gly Val Gln Asp Ser Cys
65                  70                  75                  80

Gly Cys Tyr Thr Val Ser Ser Val Leu Pro Gly Cys Ala Glu Arg Trp
                85                  90                  95

Asn Asn Gly Glu Thr Phe Thr Cys Thr Ala Thr His Pro Glu Phe Glu
            100                 105                 110

Thr Pro Leu Thr Gly Glu Ile Ala Lys Val Thr Glu Asn Thr Phe Pro
        115                 120                 125

Pro Gln Val His Leu Leu Pro Pro Ser Glu Glu Leu Ala Leu Asn
    130                 135                 140

Glu Leu Val Ser Leu Thr Cys Leu Val Arg Gly Phe Asn Pro Lys Asp
145                 150                 155                 160

Val Leu Val Arg Trp Leu Gln Gly Asn Glu Glu Leu Pro Ser Glu Ser
                165                 170                 175

Tyr Leu Val Phe Glu Pro Leu Arg Glu Pro Gly Glu Gly Ala Ile Thr
            180                 185                 190

Tyr Leu Val Thr Ser Val Leu Arg Val Ser Ala Glu Thr Trp Lys Gln
        195                 200                 205

Gly Ala Gln Tyr Ser Cys Met Val Gly His Glu Ala Leu Pro Met Ser
    210                 215                 220

Phe Thr Gln Lys Thr Ile Asp Arg Leu Ser Gly Lys Pro Thr Asn Val
225                 230                 235                 240

Asn Val Ser Val Ile Met Ser Glu Gly Asp Gly Ile Cys Tyr
                245                 250

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Gly Leu Asn Asp Ile Phe Glu Ala Gln Lys Ile Glu Trp His Glu
1               5                   10                  15